United States Patent
Steinkuhler et al.

(10) Patent No.: US 7,078,215 B2
(45) Date of Patent: Jul. 18, 2006

(54) HCV NS2/3 FRAGMENTS AND USES THEREOF

(75) Inventors: Christian Steinkuhler, Rome (IT); Michele Pallaoro, Acilia (IT); Armin Lahm, Rome (IT)

(73) Assignee: Istituto Di Ricerche Di Biologia Molecolare P. Angeletti, S.P.A., Rome (IT)

( * ) Notice: Subject to any disclaimer, the term of this patent is extended or adjusted under 35 U.S.C. 154(b) by 426 days.

(21) Appl. No.: 10/221,943

(22) PCT Filed: Mar. 14, 2001

(86) PCT No.: PCT/IB01/00527

§ 371 (c)(1),
(2), (4) Date: Sep. 17, 2002

(87) PCT Pub. No.: WO01/68818

PCT Pub. Date: Sep. 20, 2001

(65) Prior Publication Data

US 2004/0054134 A1    Mar. 18, 2004

(30) Foreign Application Priority Data

Mar. 17, 2000  (GB) ................. 0006537.5

(51) Int. Cl.
*C12N 9/50* (2006.01)
*C12N 15/33* (2006.01)
*C12N 15/57* (2006.01)
*C12Q 1/37* (2006.01)

(52) U.S. Cl. .............. 435/219; 435/23; 435/69.1; 435/69.7; 435/252.3; 536/23.2; 536/23.72

(58) Field of Classification Search .......... None
See application file for complete search history.

(56) References Cited

U.S. PATENT DOCUMENTS

| | | | |
|---|---|---|---|
| 5,837,464 A * | 11/1998 | Capon et al. ............ | 435/6 |
| 5,888,762 A | 3/1999 | Joliot et al. | |
| 6,197,536 B1 * | 3/2001 | Steinkuhler et al. ........ | 435/23 |
| 6,242,187 B1 * | 6/2001 | Capon et al. ............ | 435/6 |
| 6,280,940 B1 * | 8/2001 | Potts et al. ............ | 435/6 |
| 6,599,738 B1 * | 7/2003 | Potts et al. ............ | 435/320.1 |
| 6,790,612 B1 * | 9/2004 | Potts et al. ............ | 435/5 |
| 6,815,159 B1 * | 11/2004 | Thibeault et al. ........ | 435/5 |

FOREIGN PATENT DOCUMENTS

| WO | WO 97/08304 | 3/1997 |
|---|---|---|
| WO | WO 2001/16379 A1 * | 3/2001 |

OTHER PUBLICATIONS

Belyaev, A. et al. "Hepatitis G Virus Encodes Protease Activities Which Can Effect Processing of the Virus Putative Nonstructural Proteins", Journal of Virology, 1998, vol. 72, pp. 868-872.

(Continued)

*Primary Examiner*—Nashaat T. Nashed
*Assistant Examiner*—William W. Moore
(74) *Attorney, Agent, or Firm*—Sheldon O. Heber; Jack L. Tribble

(57) ABSTRACT

Truncated HCV NS2/3 can be produced recombinantly and renatured into functional enzyme, useful in assays for modulators of activity and HCV function.

16 Claims, 4 Drawing Sheets

Step 1. - Refold NS2/3

Figure 1:
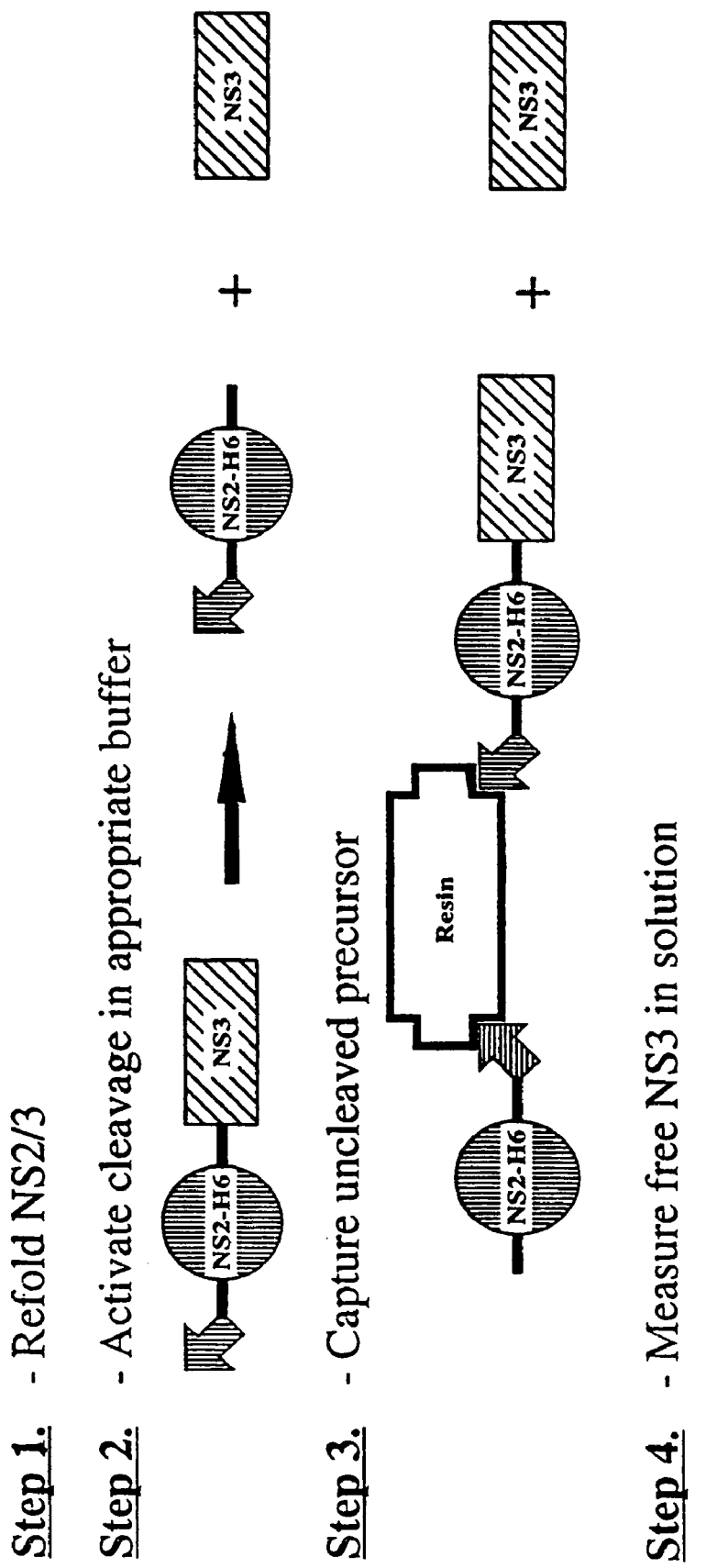

Step 2. - Activate cleavage in appropriate buffer

Step 3. - Capture uncleaved precursor

Step 4. - Measure free NS3 in solution

OTHER PUBLICATIONS

Darke, P. et al. "Inhibition of Hepatitis C Virus NS2/3 Processing by NS4A Peptides", The Journal of Biological Chemistry, 1999, vol. 274, pp. 34511-34514.

Grakoui, A. et al. "A second hepatitis C virus-encoded proteinase", Proc. Natl. Acad. Sci. USA, 1993, vol. 90, pp. 10583-10587.

Han, D .et al. "Identification of the protease domain in NS3 of hepatitis C virus", Journal of General Virology, 1995, vol. 76, pp. 985-993.

Han, J. et al. "Group specific sequences and conserved secondary structures at the 340 end of HCV genome and is implication for viral replication", Nucleic Acids Research, 1992, vol. 20, pp. 3520.

Hijikata, M. et al. "Two Distinct Proteinase Activities Required for the Processing of a Putative Nonstructural Precursor Protein of Hepatitis C Virus", Journal of Virology, 1993, vol. 67, pp. 4665-4675.

Hotta, H. et al. "Analysis of the core and E1 envelope region sequences of a novel variant of hepatitis c virus obtained in Indonesia", Archives of Virology, 1994, vol. 136, pp. 53-62.

Inchauspe, G. et al. "Genomic structure of the human prototype strain H of hepatitis C virus: Comparison with American and Japanese isolates", Proc. Natl. Acad. Sci. USA, 1991, vol. 88, p. 10292-10296.

Kato, N. et al. "A Structural Protein Encoded by the 5' Region of the Hepatitis C Virus Genome Efficiently Detects Viral Infection", Jpn. J. Cancer Res., 1990, vol. 81, pp. 1092-1094.

Kato, N. et al. "Molecular cloning of the human hepatitis C virus genome from Japanese patients with non-A, non-B hepatitis", Proc. Natl. Acad. Sci. USA, 1990, vol. 87, pp. 9524-9528.

Kato, N. et al. "Molecular structure of the Japanese hepatitis C viral genome", FEBS Letters, 1991, vol. 280, pp. 325-328.

Kim, J. et al. "Hepatitis C virus NS3 RNA helicase domain with a bound oligonucleotide: the crystal structure provides insights into the mode of unwinding", Strucure, 1998, vol. 6, pp. 89-100.

Kolykhalov, A. et al. "Hepatitis C Virus-Encoded Enzymatic Activities and Conserved RNA Elements in the 3' Nontranslated Region Are Essential for Virus Replication In Vivo", Journal of Virology, 2000, vol. 74, pp. 2046-2051.

Kolykhalov, A. et al. "Transmission of Hepatitis C by Intrahepatic Inoculation with Transcribed RNA", Science, 1997, vol. 277, pp. 570-574.

Mink, M. et al. "Characterization and Mapping of a B-Cell Immunogenic Domain in Hepatitis C Virus E2 Glycoprotein Using a Yeast Peptide Library", Virology, 1994, vol. 200, pp. 246-255.

Miyakawa, Y. et al. "Classifying hepatitis C virus genotypes", Molecular Medicine Today, 1995, vol. 1, pp. 20-25.

Pallaoro, M. et al. "Characterization of the Hepatitis C Virus NS2/3 Processing Reaction by Using a Purified Precursor Protein", Journal of Virology, 2001, vol. 75, pp. 9939-9946.

Pieroni, L. et al. "In Vitro Study of the NS2-3 Protease of Hepatitis C Virus", Journal of Virology, 1997, vol. 71, pp. 6373-6380.

Reed, K. et al. "Hepatitis C Virus-Encoded NS2-3 Protease: Cleavage-Site Mutagenesis and Requirements for Bimolecular Cleavage", Journal of Virology, 1995, vol. 69, pp. 4127-4136.

Santolini, E. et al. "The NS2 Protein of Hepatitis C Virus Is a Transmembrane Polypeptide", Journal of Virology, 1995, vol. 69, pp. 7461-7471.

Tokita, H. et al. "Hepatitis C virus variants from Jakarta, Indonesia classifiable into novel genotypes in the second (2e and 2f), tenth (10a) and eleventh (11a) genetic groups", Journal of General Virology, 1996, vol. 77, pp. 293-301.

Wilkinson, C. "Hepatitis C virus NS2-3 proteinase", Biochemical Society Transactions, 1997, vol. 25, pp. S611.

Wu, Z. et al. "Mechanism of autoproteolysis at the NS2-NS3 junction of the hepatitis C virus polyprotein", TIBS, 1998, vol. 23, pp. 92-94.

Yao, N. et al. "Structure of the hepatitis C virus RNA helicase domain", Nature Structural Biology, 1997, vol. 4, pp. 463-467.

* cited by examiner

HCV NS2/3 FRAGMENTS AND USES THEREOF

The present invention relates to assays, screening methods, polypeptides, mimetics, and methods of use based on a polypeptide derived from Hepatitis C virus (HCV) NS2/3 protease.

The hepatitis C virus (HCV) is the major causative agent of parenterally-transmitted and sporadic non-A, non-B hepatitis (NANB-H). Some 1% of the human population of the planet is believed to be affected. Infection by the virus can result in chronic hepatitis and cirrhosis of the liver, and may lead to hepatocellular carcinoma. Currently no vaccine nor established therapy exists, although partial success has been achieved in a minority of cases by treatment with recombinant interferon-α, either alone or in combination with ribavirin. There is therefore a pressing need for new and broadly-effective therapeutics.

Several virally-encoded enzymes are putative targets for therapeutic intervention, including an autoprotease (NS2-3), a serine protease (NS3), a helicase (NS3), and an RNA-dependent RNA polymerase (NS5B).

The NS3 protease domain is located at the N-terminal of the NS3 protein, and is responsible for an intramolecular cleavage at the NS3/4A site and for downstream intermolecular processing at the NS4A/4B, NS4B/5A and NS5A/5B junctions.

NS3 is formed by the proteolytic cleavage of the precursor molecule NS2/3, generating the mature N-terminal of NS3. This reaction is auto-catalysed by the NS2/3 precursor molecule itself.

The auto-catalytic activity of the NS2/3 protease is believed to be essential for the replication of HCV (Kolykhalov, A. et al. (2000) J. Virol. 74 2046–2051)and therefore represents a potentially important therapeutic target in the treatment of HCV infection.

The precise mechanism of NS2/3 cleavage is unknown but it is known to be an intra-molecular, possibly co-translational, reaction that is catalyzed by the NS2/3 proteolytic activity (Wu et al., TIBS 23, 92–94, 1998). Because the activity is stimulated by the addition of metal ions such as Zn or Cd to in vitro translation assays, the enzyme has been tentatively classified as a metalloprotease. Study of the NS2/3 precursor has been complicated by its auto-proteolytic activity, insolubility and instability.

No in vitro assays using a purified NS2/3 protease have yet been reported. The insolubility and instability of the protease and its auto-catalytic activity have blocked the development of such assays.

NS2/3 protease activity in cell-free translation systems and in transfected cells has been described by Grakoui et al (1993)PNAS 90, 10583–10587, and Hijikata et al.(1993) J. Virol 67, 4665–4675. The cleavage site of the NS2/3 protease was found by these groups to be between residues 1026 and 1027 of the HCV polypeptide and cleavage was shown to be Zn-dependent. Cys993 and His952 were determined to be essential for cleavage and sequences between residues 827 and 1186–1207 were also required for activity. A trans-cleavage activity was also identified. All the studies conducted by these groups were on cells or cell extracts.

Reed et al. (1995) J. Virol. 69, 4127–4136 reported the trans-cleavage activity and trans-inhibition of cleavage of the NS2/3 protease in cell-based systems and also described the sequence specificity of the cleavage reaction.

Pieroni et al (1997) J. Virol 71, 6373–6380 described the production of NS2/NS3 precursor in a latent form in a cell-free translation system and also its reactivation by the addition of detergent. However, the system described did not involve purified enzyme.

Cleavage at the NS2/3 site requires both the NS3 protease domain (but not its serine protease activity) and the NS2 protein that starts at residue 810 of the HCV NS2/3 precursor. The first ~100 residues of NS2 are highly hydrophobic and may be associated with the ER membrane in infected cells. This hydrophobic portion may be responsible for the poor solubility of the protein. Deletions of the N-terminal region up to residue 923 have been shown to abolish activity.

Based on the experimental work and discussion herein, the present invention in various aspects is based on the obtaining NS2/3 protease polypeptides that start at a residue from 903 to 913 i.e. 903, 904, 905, 906, 907, 908, 909, 910, 911, 912, or 913, and terminate at residue 1206, residue 1657 or a residue between 1206 and 1657.

Surprisingly, these truncated polypeptides retain the auto-proteolytic activity of the full length protease but are capable of undergoing purification in the precursor form without undergoing auto-cleavage. Furthermore, it is a dimeric form of the polypeptide which is shown to be responsible for the auto-proteolytic activity. The active polypeptide is therefore capable of dimerisation to generate the auto-proteolytic activity.

The provision of an active precursor molecule in turn enables the provision of assays and screening methods for agents that can modulate, especially inhibit, the auto-proteolytic activity of the NS2/3 precursor and which therefore have therapeutic potential in the treatment of HCV.

Various aspects of the present invention provide for a polypeptide which has auto-proteolytic activity and which is capable of being expressed in an inactive form without self-cleavage and subsequently activated. The auto-proteolytic form of the polypeptide may be a homo-dimer.

The present invention provides a polypeptide or a polypeptide fragment having an N-terminal boundary between residues 903 and 913 and a C-terminal boundary at or between residues 1206 and 1657. The polypeptide or polypeptide fragment may therefore be truncated at its C terminal or it may comprise the complete NS3 sequence. Preferably, the polypeptide or polypeptide fragment includes the complete protease domain of NS3. In preferred embodiments, the C-terminal boundary is at residue 1206.

References herein to the HCV polyprotein sequence and residues therein refer to one or more of the HCV polyprotein sequences from the databases as follows: HCV J strain polyprotein, Swissprot Acc No:P26662; HCV H strain polyprotein, Swissprot Acc No: P27958; H77 strain polyprotein, Translated-Genbank Acc. No AAB66324 or TREMBL Acc. No.036579. However, isolates of other HCV strains and genotypes may also be employed in accordance with the present invention.

HCV isolates may be derived from HCV of 1a, 1b, 1c, 2a, 2b, 2c, 2d, 2e, 2f, 3a, 3b, 3c, 3d, 3e, 3f, 4a, 4b, 4c, 4d, 5a, 6a, 6b, 7a, 7b, 8a, 8b, 9a, 9b, 9c, 10a or 11a genotype, as described in Tokita, M. et al J. Gen. Virol.(1996) 77, 293–301 and Myakawa, Y. et al Molecular Med. Today (1995) 1, 20–25, or derived from HCV of the H-FDA, H-AP, HCV-1, HCV-J, HCV-BK, HC-J6, HCV-T, HC-J8 or HCV-JT strains described in Grakoui et al Proc. Natl. Acad. Sci. USA (1993) 90, 10583–10587.

The present invention also provides a polypeptide or a polypeptide fragment consisting essentially of an amino acid sequence starting at residue 903, 913 or a residue located between these residues and ending at residue 1206, 1657 or a residue located between these residues. The polypeptide or polypeptide fragment may therefore be truncated at its C terminal or it may comprise the complete NS3 sequence. Preferably, the polypeptide or polypeptide fragment includes the complete protease domain of NS3.

The polypeptide or polypeptide fragment may, for example, have an N-terminal boundary at residue 903, 904, 905, 906, 907, 908, 909, 910, 911, 912 or 913 of the HCV polyprotein and a C terminal at or between residues 1206 and 1657, for example, residue 1250, 1300, 1350, 1400, 1450, 1500, 1550, 1600 or 1650.

A polypeptide may be in isolated and/or purified form, free or substantially free of material with which it may be associated, such as other polypeptides, or (for example if produced by expression in a prokaryotic cell) lacking in native glycosylation, e.g. unglycosylated.

Polypeptides which are amino acid sequence variants, derivatives or mutants are also provided by the present invention. A polypeptide which is a variant, derivative or mutant may have an amino acid sequence which differs from the corresponding sequence of the HCV polyprotein (for example, Swissprot Acc No:P26662 described above) by one or more of addition, substitution, deletion and insertion of one or more amino acids but has auto-proteolytic activity in a dimeric form and can be expressed in an inactive form and subsequently activated.

Amino acid sequences may consist of between 293 and 754 residues and correspond to the sequence starting at or between residues 903 and 913 and extending to a sequence at or between residues 1206 and 1657 of the native HCV protease. More preferably, sequences may consist of between 293 and 303 residues, corresponding to the sequence starting at or between residues 903 and 913 and extending to residue 1206 of the native HCV protease.

A polypeptide which is an amino acid sequence variant, derivative or mutant of the corresponding region of the HCV polyprotein sequence may comprise an amino acid sequence which shares greater than about 60% similarity, greater than about 70% similarity, greater than about 80% similarity, greater than about 90% similarity, greater than about 95% similarity or substantially identical with the amino acid sequence of HCV NS2/3 polyprotein. Amino acid similarity is generally defined with reference to the algorithm GAP (Genetics Computer Group, Madison, Wis.) as noted above, or the TBLASTN program, of Altschul et al. (1990) J. Mol. Biol. 215: 403–10. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a sequence referred to herein by insertion, addition, substitution or deletion of 1 amino acid, 2, 3, 4, 5–10, 10–20 20–30, 30–50, 50–100, 100–150, or more than 150 amino acids.

Sequence comparison may be made over the full-length of the relevant sequences shown herein.

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Homology may be taken over the full-length of a sequence or over a part, such as 20, 30, 40, 50, 60, 70, 80, 90, 100, 120, 150, 200 contiguous nucleotides or amino acids. That two nucleotide sequences are said to share "homology" or be "homologous" is based on sequence comparison. Any phylogenetic relationship is irrelevant for this. Those skilled in the art routinely refer to homology between nucleotide sequences with no implication for evolutionary origin. Two homologous nucleotide sequences may also be said to be "similar" or have a certain percentage similarity or a certain percentage identity.

In general it is not critical which of the various standard algorithms are used to determine how homologous two nucleotide sequences are with one another. A preferred algorithm may be GAP, which uses the alignment method of Needleman and Wunsch (J. Mol. Biol. (1970) 48, 443–453) and is included in the Program Manual or the Wisconsin Package, Version 8, September 1994, Genetics Computer Group, 575 Science Drive, Madison, Wis., USA). In the absence of instructions to the contrary, the skilled person would understand to use the default parameters with the aim of maximizing alignment, with a gap creation penalty=12 and gap extension penalty=4.

Similarity or homology (the terms are used interchangeably) or identity may be as defined and determined by the TBLASTN program, of Altschul et al. (1990) J. Mol. Biol. 215: 403–10, or BestFit, which is part of the Wisconsin Package, Version 8, September 1994, (Genetics Computer Group, 575 Science Drive, Madison, Wis., USA, Wisconsin 53711). Preferably sequence comparisons are made using FASTA and FASTP (see Pearson & Lipman, 1988. Methods in Enzymology 183: 63–98) Parameters are preferably set, using the default matrix, as follows: Gapopen (penalty for the first residue in a gap): −12 for proteins/−16 for DNA; Gapext (penalty for additional residues in a gap): −2 for proteins/−4 for DNA; KTUP word length: 2 for proteins/6 for DNA.

Nucleic acid sequence homology may be determined by means of selective hybridisation between molecules under stringent conditions.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein >SSC==0.15 M sodium chloride; 0.15 M sodium citrate; pH 7), 5× Denhardt=s reagent, 0.5–1.0% SDS, 100 µg/ml denatured, fragmented salmon sperm DNA, 0.05% sodium pyrophosphate and up to 50% formamide. Hybridization is carried out at 37–42□ C for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m=81.5°$ C.+16.6 Log [Na+]+0.41 (% G+C)−0.63 (% formamide)−600/#bp in duplex.

As an illustration of the above formula, using [Na+]=[0.368] and 50–% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridization gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60☐ C in 0.1×SSC, 0.1% SDS.

The skilled person can use the techniques described herein and others well known in the art to produce large amounts of polypeptide, for instance by expression from encoding nucleic acid.

According to another aspect of the present invention there is provided a nucleic acid molecule which has a nucleotide sequence encoding a polypeptide having an amino acid sequence as described above.

The coding sequence may encode the HCV NS2/3 protease encoded by the genome of the HCV J strain, recorded as Genbank Acc. No. D90208 and set forth in SEQ ID NO:33 herein; or the HCV H strain, recorded as Genbank Acc. No. M67463 and set forth in SEQ ID NO:34 herein; or the HCV H77 strain recorded as Genbank Acc. AF009606 and set forth in SEQ ID NO:35 herein; or it may be a mutant, variant, derivative of the coding sequence. The sequence may differ from the HCV NS2/3 nucleotide sequence by a change which is one or more of addition, insertion, deletion and substitution of one or more nucleotides of the sequence. Changes to a nucleotide sequence may result in an amino acid change at the protein level, or not, as determined by the genetic code.

Thus, nucleic acid according to the present invention may include a sequence different from the nucleic acid sequence of HCV NS2/3 yet encode a polypeptide with the same amino acid sequence.

Generally, nucleic acid according to the present invention is provided as an isolate, in isolated and/or purified form, or free or substantially free of material with which it is naturally associated, such as free or substantially free of nucleic acid flanking the gene in the viral genome, except possibly one or more regulatory sequence(s) for expression. Nucleic acid may be wholly or partially synthetic and may include genomic DNA, cDNA or RNA. The coding sequence shown herein is a DNA sequence. Where nucleic acid according to the invention includes RNA, reference to the sequence shown should be construed as encompassing reference to the RNA equivalent, with U substituted for T.

Nucleic acid may be provided as part of a replicable vector, and also provided by the present invention are a vector including nucleic acid as set out above, particularly any expression vector from which the encoded polypeptide can be expressed under appropriate conditions, and a host cell containing any such vector or nucleic acid. An expression vector in this context is a nucleic acid molecule including nucleic acid encoding a polypeptide of interest and appropriate regulatory sequences for expression of the polypeptide, in an in vitro expression system, e.g. reticulocyte lysate, or in vivo, e.g. in eukaryotic cells such as COS or CHO cells or in prokaryotic cells such as E. coli. Cells comprising vectors as described above are a further aspect of the present invention.

Generally, nucleic acid according to the present invention is provided as an isolate, in isolated and/or purified form, or free or substantially free of material with which it is naturally associated, such as free or substantially free of nucleic acid flanking the gene in the (e.g. viral) genome, except possibly one or more regulatory sequence(s) for expression. Nucleic acid may be wholly or partially synthetic and may include genomic DNA, cDNA or RNA.

Nucleic acid sequences encoding the polypeptides of the present invention may be readily prepared by the skilled person using the information and references contained herein and techniques known in the art (for example, see Sambrook, Fritsch and Maniatis, Molecular Cloning, A Laboratory Manual, Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences. DNA encoding the polypeptides may be generated and used in any suitable way known to those of skill in the art, including taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers.

Modifications to a nucleic acid sequence may be made, e.g. using site directed mutagenesis, to lead to the production of modified polypeptide, e.g. to take account of codon preference in the host cells used to express the nucleic acid.

In order to obtain expression of the nucleic acid sequences of the invention, the sequences may be incorporated in a vector having one or more control sequences operably linked to the nucleic acid to control its expression. Vectors may be chosen or constructed, They may contain appropriate regulatory sequences, including promoter sequences, terminator fragments, polyadenylation sequences, enhancer sequences, marker genes and other sequences as appropriate, e.g. nucleic acid sequences so that the polypeptide or peptide is produced as a fusion and/or nucleic acid encoding secretion signals so that the polypeptide produced in the host cell is secreted from the cell. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Polypeptide may then be obtained by transforming the vectors into host cells in which the vector is functional, culturing the host cells so that the polypeptide is produced and recovering the polypeptide from the host cells or the surrounding medium.

A further aspect of the present invention provides a host cell containing heterologous nucleic acid as disclosed herein.

Systems for cloning and expression of polypeptides in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A further aspect provides a method which includes introducing a nucleic acid molecule of the invention into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. If the polypeptide is expressed coupled to an appropriate signal leader peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

In light of the above, the present invention also provides a method of making a truncated HCV NS2/3 protease polypeptide of the present invention, the method including expression from nucleic acid encoding the polypeptide. This may conveniently be achieved by growing a host cell containing the nucleic acid in culture under appropriate conditions which cause or allow expression of the HCV NS2/3 protease polypeptide whilst minimising auto-proteolysis. Preferred conditions include a Zn-depleted or low Zn medium. This hinders the folding of the NS3 portion of the precursor molecule, thereby impeding auto-processing and driving the formation of insoluble protein that accumulates in inclusion bodies.

Methods for the purification of insoluble proteins expressed in inclusion bodies are well-known to persons skilled in the art. Conveniently, gel filtration is employed under denaturing conditions followed by reversed phase chromatography.

The denatured, purified protein may be renaturated after purification by adjusting the conditions to allow refolding. This is preferably achieved-in a refolding buffer in which the chaotropic agent (guanidine) concentration has been reduced by dialysis to a residual concentration of 0.75 M, ionic strength is greater than 200 mM NaCl and the concentration of protein is less than 100 ug/ml. Refolded, soluble protein can be measured by analysing the supernatant after ultracentrifugation of the refolded sample.

Refolded, soluble protein may be activated by altering the buffer conditions. A suitable buffer for activation of the protease may include the following components:

Ionic strength equivalent to at least 50 mM, preferably at least 100 mM, or at least 150 mM NaCl, for example 200 mM, 250 mM or 300 mM NaCl;

10–60% glycerol, preferably 20–50% glycerol, for example 30%, 40% or 50% glycerol;

0.5%–3% CHAPS, preferably 1–2% CHAPS, for example 1%, 1.5% or 2% CHAPS;

pH 6.5–8.5, preferably pH 7–8, for example pH 7, 7.5 or 8;

1–100 mM reducing agent (e.g. cysteine or DTT), preferably 1–10 mM reducing agent, for example, 1 mM, 3 mM, 5 mM or 10 mM reducing agent;

1–100 µM $Zn^{++}$, preferably 5–50 µM $Zn^{++}$, for example 30 µM, 40 µM or 50 µM $Zn^{++}$.

One method of activation is to reduce the protein concentration to 2.5 µg/ml or less in a buffer containing 50 mM TRIS pH 7.5, 50% glycerol, 2% CHAPS, 250mM NaCl, 3mM DTT, 30 µM $Zn^{++}$(See Example 7).

Various aspects of the present invention provide for assays and methods of screening for and/or obtaining/identifying a substance which modulates, e.g. inhibits, reduces or interferes with, the activity of the HCV NS2/3 protease, and for the use of HCV NS2/3 protease polypeptides of the present invention in these screening methods and assays. The activity of the protease may be modulated by promotion or inhibition of dimerisation.

A screening or assay method for identifying an agent which can modulate the activity of the HCV NS2/3 protease, may include:

(a) bringing a test agent into contact with an HCV NS2/3 protease polypeptide of the present invention; and (b) determining the HCV NS2/3 protease activity.

The HCV NS2/3 protease polypeptide which is brought into contact with the test agent may be in the monomeric or the dimeric form. Where the polypeptide is monomeric, the test agent may modulate the formation of the dimeric form, the proteolytic activity of the dimer, or both. Where the polypeptide is dimeric, the test agent may modulate the formation of the monomer form, the proteolytic activity of the dimer, or both.

Modulation of the formation of the dimeric or monomeric form may be achieved by influencing the dynamic equilibrium between the two forms.

A screening or assay method may additionally include the step of activating the HCV NS2/3 protease. This activation may be achieved by changing the buffer conditions.

HCV NS2/3 protease polypeptides of the present invention may form homo-dimers so an agent which affects the dimerisation of the polypeptide may modulate the auto-proteolytic activity.

Activity of an HCV NS2/3 protease polypeptide of the present invention may be determined by assessing the proportion of the polypeptide in the active dimeric form.

Accordingly, a screening or assay method for identifying an agent which can modulate the activity of the HCV NS2/3 protease, may include:

(a) bringing a test agent into contact with an HCV NS2/3 protease polypeptide of the present invention; and (b) determining dimerisation of the HCV NS2/3 protease polypeptide.

Dimerisation may be determined by standard methods well-known to a skilled person, for example by the use of gel filtration chromatography, antibodies or the dependence of the cleavage kinetics on the protein concentration.

A related aspect of the present invention provides the use of an HCV NS2/3 protease polypeptide of the present invention for determining the presence in a test sample of an agent which has the ability to modulate the activity of the native HCV NS2/3 protease.

A method for determining the presence in a test sample of an agent which has the ability to modulate the activity of the HCV NS2/3 protease, may include:
(a) bringing an HCV NS2/3 protease polypeptide of the present invention into contact with the test sample; and
(b) determining activity of the HCV NS2/3 protease polypeptide.

The method may additionally include the step of activating the HCV NS2/3 protease polypeptide. This activation may be achieved by changing the buffer conditions.

Activating the polypeptide may comprise promoting the formation of homo-dimers of the polypeptide.

An agent which can modulate the activity of the HCV NS2/3 protease may affect the formation of the active dimeric form.

A method for determining the presence in a test sample of an agent which has the ability to modulate the dimerisation of the HCV NS2/3 protease, may include:
(a) bringing an HCV NS2/3 protease polypeptide of the present invention into contact with the test sample; and
(b) determining HCV NS2/3 protease activity.

Activity in the presence of a test substance may be compared with activity of the HCV NS2/3 protease polypeptide in comparable reaction medium and conditions in the absence of a test substance. A test substance able to modulate the activity may thereby be identified. A difference in the activity of the HCV NS2/3 protease polypeptide between the treated and untreated conditions is indicative of a modulating effect of the relevant test substance(s). Activity may be related to the extent of dimerisation of the polypeptide.

The relevant test substance may achieve a modulating effect by affecting (i.e. reducing or increasing) the dimerisation of an HCV NS2/3 protease polypeptide of the present invention. The presence of a modulating effect may be determined by assessing the dimerisation of the HCV NS2/3 protease polypeptide.

A method for determining the presence in a test sample of an agent which has the ability to modulate the dimerisation of the HCV NS2/3 protease, may include:
(a) bringing an HCV NS2/3 protease polypeptide of the present invention into contact with the test sample; and
(b) determining dimerisation of the HCV NS2/3 protease polypeptide.

Activity may be determined by any suitable method. Examples of such methods include an HPLC based approach in which activated enzyme in incubated for a fixed time and the uncleaved precursor separated from the products on an HPLC column, the amount of product as measured by fluorescence being related to the activity. Another approach involves separating the NS3 cleavage product from the NS2/3 precursor and the NS2 product by means of 5' tags and quantifying the amount of NS3 by a standard fluorimetric or radiometric assay.

A method for determining the presence in a test sample of an agent which has the ability to modulate the activity of the HCV NS2/3 protease, may include quantifying the activity of an HCV NS2/3 protease polypeptide of the present invention and/or the amount of said agent in the sample and/or the amount of dimerisation of the HCV NS2/3 protease polypeptide.

Where appropriate, one or more controls may be included in the assays and methods described herein. Suitable controls would be readily employed by a skilled person.

Agents which modulate e.g. increase or potentiate activity of the HCV NS2/3 protease may be identified using conditions which, in the absence of a positively-testing agent, destroy or reduce activity.

Methods of determining the presence of, and optionally quantifying the amount of, an agent in a test sample which has the ability to modulate the activity of HCV NS2/3 protease may have a diagnostic purpose, e.g. in the evaluation of a therapy to treat a condition associated with HCV infection.

A screening or assay method may include purifying and/or isolating a test substance (e.g. an agent to be tested for the ability to modulate HCV NS2/3 protease activity) from a mixture or extract, i.e. reducing the content of at least one component of the mixture or extract, e.g. a component with which the test substance is naturally associated. The screening or assay method may include determining the ability of one or more fractions of a test mixture or extract to modulate the activity of the HCV NS2/3 protease. The purifying and/or isolating may employ any method known to those skilled in the art.

The precise format of any of the screening or assay methods of the present invention may be varied by those of skill in the art using routine skill and knowledge. The skilled person is well aware of the need to employ appropriate control experiments.

In any assay method according to the invention, the amount of test substance or compound which may be added to an assay of the invention will normally be determined by trial and error depending upon the type of compound used. Typically, from about 0.001 nM to 1 mM or more concentrations of putative modulator/inhibitor compound may be used, for example from 0.01 nM to 100 µM, e.g. 0.1 to 50 µM, such as about 10 µM. Greater concentrations may be used when a peptide is the test substance. Even a molecule which has a weak effect may be a useful lead compound for further investigation and development.

A compound or agent identified by any one of the methods provided by the present invention may be isolated and/or purified and/or further investigated and/or manufactured. Various methods and uses of such compounds are discussed elsewhere herein. The present invention thus provides methods of identifying agents which have the ability to modulate the activity of HCV NS2/3 protease.

An agent or substance employed in a method in accordance with the present invention may be a natural or synthetic chemical compound and may be an organic, inorganic, peptide, nucleic acid or other molecule. Suitable compounds which may be screened include natural or synthetic chemical compounds used in drug screening programmes. Extracts of plants, microbes or other organisms, which contain several characterised or uncharacterised components may also be used.

It is worth noting that combinatorial library technology provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

One class of putative modulators comprises peptide fragments derived from HCV NS2/3 protease polypeptides of the present invention, or alleles, mutants or derivatives of such fragments. Peptide fragments of from 5 to 40 amino acids, for example from 6 to 10 amino acids from the regions of the polypeptide where cleavage occurs or which are responsible for activity, may be tested for their ability to inhibit auto-proteolysis.

Other suitable peptides are those which modulate the activity of an HCV NS2/3 protease polypeptide of the present invention and which have a length of 50–55, 55–60, 60–65, 65–70, 70–75, 75–80, 80–85, 85–90, 90–95, 95–100, or more than 100 amino acids.

Other suitable peptides are those which inhibit the dimerisation of an HCV NS2/3 protease polypeptide of the present invention and which have a length of 50–55, 55–60, 60–65, 65–70, 70–75, 75–80, 80–85, 85–90, 90–95, 95–100, or more than 100 amino acids.

Nucleic acid encoding such fragments, vectors and host cells containing such nucleic acid, and methods of expressing nucleic acid encoding such fragments are further aspects of the present invention.

Other candidate inhibitor compounds may be based on modelling the 3-dimensional structure of the HCV NS2/3 protease polypeptide and using rational drug design to provide potential inhibitor compounds with particular molecular shape, size and charge characteristics.

Following identification of a substance which modulates or affects protease activity, the substance may be investigated further. Furthermore, it may be manufactured and/or used in preparation, i.e. manufacture or formulation, of a composition such as a medicament, pharmaceutical composition or drug. These may be administered to individuals.

In various aspects, the present invention provides a modulator identified by a screening method of the invention, e.g. a substance which inhibits or diminishes, increases or potentiates activity of the HCV NS2/3 protease.

The modulator may be purified and/or investigated further and/or manufactured, following identification. A modulator may be used to obtain peptidyl or non-peptidyl mimetics, e.g. by methods well known to those skilled in the art and discussed herein. It may be used in a therapeutic context as discussed below.

Antibodies directed to an HCV NS2/3 protease polypeptide of the present invention form a further class of putative inhibitor compounds. Candidate inhibitor antibodies may be characterised and their binding regions determined to provide single chain antibodies and fragments thereof which are responsible for affecting the protease activity.

Antibodies may be obtained using techniques which are standard in the art. Methods of producing antibodies include immunising a mammal (e.g. mouse, rat, rabbit, horse, goat, sheep or monkey) with an HCV NS2/3 protease polypeptide of the present invention. Antibodies may be obtained from immunised animals using any of a variety of techniques known in the art, and screened for modulation of HCV NS2/3 activity using an HCV NS2/3 protease polypeptide of the present invention. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for an HCV NS2/3 protease polypeptide of the present invention may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with an HCV NS2/3 protease polypeptide of the present invention (or fragments thereof), or may be one constructed using sequences obtained from an organism which has been exposed to the antigen of interest. Candidate antibodies may be screened for modulation of HCV NS2/3 activity using the NS2/3 protease polypeptide.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

Antibodies may also be used in purifying and/or isolating HCV NS2/3 protease polypeptides of the present invention, for instance, following production of the polypeptide by expression from encoding nucleic acid therefor. Antibodies may be useful in a therapeutic context (which may include prophylaxis) to disrupt activity of the HCV NS2/3 protease with a view to inhibiting the replication of HCV and thereby reducing or preventing HCV infection. Antibodies can for instance be micro-injected into cells or tissues or administered systemically. Antibodies may be employed in accordance with the present invention for other therapeutic and non-therapeutic purposes which are discussed elsewhere herein.

In a further aspect, the present invention provides the use of an agent which is capable of modulating the activity of an HCV NS2/3 protease polypeptide of the present invention, in a method of designing a peptide or non-peptidyl mimetic of the compound, which mimetic is able to modulate the activity of HCV NS2/3 protease. The agent used in such a method may be an agent identified using methods according to the present invention.

The present invention similarly provides for the use of an HCV NS2/3 protease polypeptide of the present invention in a method of designing a peptide or non-peptidyl mimetic of a HCV NS2/3 protease, which mimetic is able to modulate the activity of the HCV NS2/3 protease.

Accordingly, the present invention provides a method of designing a mimetic of a compound which has the biological activity of modulating the activity of HCV NS2/3 protease, as determined by methods of the present invention, or a method of designing a mimetic of an HCV NS2/3 protease polypeptide of the present invention which has the biological activity of modulating the activity of HCV NS2/3 protease, as determined by methods of the present invention, said method comprising:
  (i) analysing a substance having the biological activity to determine the amino acid residues essential and important for the activity to define a pharmacophore; and,
  (ii) modelling the pharmacophore to design and/or screen candidate mimetics having the biological activity.

Suitable modelling techniques are known in the art. Such techniques enable the study of the interaction between an HCV NS2/3 protease polypeptide of the present invention and a modulating compound and to design compounds which contain functional groups arranged in such a manner that they could reproduce that interaction.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, for instance compounds of the present invention that are peptides may not be well suited as active agents for oral compositions as they tend to be quickly degraded by proteases in the alimentary canal.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of the above approach, the three-dimensional structure of a ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by any of the approaches described herein may be used in the assay methods of the present invention to determine whether they have the ability to modulate the activity of the HCV NS2/3 protease.

Mimetics obtained by a method of the invention form a further aspect of the invention.

As used herein, a variant of a stated amino acid sequence may differ by one or more amino acid residues from that sequence, by one or more of addition, insertion, deletion and substitution of one or more amino acid residues. It may include 1, 2, 3, 4, 5, or greater than 5 amino acid alterations such as substitutions with respect to the stated sequence.

Such a variant of an HCV NS2/3 protease polypeptide of the present invention, which has a sequence disclosed herein, may, in certain embodiments, be the same length or shorter than that sequence. In other embodiments, the HCV NS2/3 protease polypeptide of the present invention (or a variant thereof) may be included in a larger polypeptide particularly where the HCV NS2/3 protease polypeptide is fused to a heterologous or foreign sequence. For example, 1, 2, 3, 4 or 5, 10, 20 or more additional amino acid residues, heterologous to a native form of the specific HCV NS2/3 protease polypeptide, may be included at one end or both ends of the HCV NS2/3 protease polypeptide.

Derivatives of polypeptides include the polypeptide linked to a coupling partner, e.g. an effector molecule, a label, a drug, a toxin and/or a carrier or transport molecule, and/or a targeting molecule such as an antibody or binding fragment thereof or other ligand. Techniques for coupling to both peptidyl and non-peptidyl coupling partners are well known in the art. In one embodiment, the carrier molecule is a 16 amino acid peptide sequence derived from the homeodomain of Antennapedia (e.g. as sold under the name "Penetratin"), which can be coupled to a peptide via a terminal Cys residue. The "Penetratin" molecule and its properties are described in WO 91/18981.

HCV NS2/3 protease polypeptides of the present invention and/or peptide modulating agents may be generated wholly or partly by chemical synthesis, in accordance with well-established techniques, such as standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, N.Y. (1984); and Applied Biosystems 430A Users Manual, ABI Inc., Foster City, Calif.), or they may be prepared in solution, by the liquid phase method or by any combination of solid-phase, liquid phase and solution chemistry.

The invention further provides various therapeutic methods and uses of one or more substances selected from (i) a compound identified in accordance with a method of the invention which is able to modulate the activity of the HCV NS2/3 protease; (ii) a mimetic of any of the above substances which is able to modulate the activity of the HCV NS2/3 protease.

The therapeutic/prophylactic purpose of such a method or use may be the modulation, e.g. disruption or interference, of the activity of the HCV NS2/3 protease, thereby to disrupt the replication of HCV and hence reduce or prevent HCV infection.

In various further aspects the present invention thus provides a pharmaceutical composition, medicament, drug or other composition for such a purpose, the composition comprising one or more of those substances, the use of such a substance in a method of medical treatment, a method comprising administration of such a substance or composition to a patient, e.g. for treatment(which may include preventative treatment) of a medical condition, e.g. a condition associated with HCV infection, use of such a substance in the manufacture of a composition, medicament or drug for administration for such a purpose, e.g. for treatment of a condition associated with HCV infection, and a method of making a pharmaceutical composition comprising admixing such a substance with a pharmaceutically acceptable excipient, vehicle or carrier, and optionally other ingredients.

The substances may be used as sole active agents or in combination with one another or with any other active substance.

Whatever the substance used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A substance or composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The substance or composition may be administered in a localised manner to a desired site or may be delivered in a manner in which it targets particular cells.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering such substances directly, they may, where the modulating substances are polypeptides, be produced in the target cells by expression from an encoding nucleic acid introduced into the cells, e.g. from a viral vector. The vector may be targeted to the specific cells to be treated, or it may contain regulatory elements which are switched on more or less selectively by the target cells.

Nucleic acid encoding the substance e.g. a polypeptide able to modulate the activity of the HCV NS2/3 protease may thus be used in methods of gene therapy, for instance in treatment of individuals, e.g. with the aim of preventing or curing (wholly or partially) a disorder associated with HCV infection.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors in gene therapy other known methods of introducing nucleic acid into cells includes mechanical techniques such as microinjection, transfer mediated by liposomes and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

An agent or substance having an ability to modulate the activity of the HCV NS2/3 protease or a nucleic acid molecule which encodes a polypeptide having that ability, may be provided in a kit, e.g. sealed in a suitable container which protects its contents from the external environment. Such a kit may include instructions for use.

In still further aspects the present invention provides for the purification of a polypeptide, protein or other substance which has the ability to modulate the activity of the HCV NS2/3 protease. The invention also provides for a purified protein, polypeptide or other substance which has the ability to modulate the activity of the HCV NS2/3 protease. The purified protein, polypeptide or other substance may be about 10% pure, more preferably about 20% pure, more preferably about 30% pure, more preferably about 40% pure, more preferably about 50% pure, more preferably about 60% pure, more preferably about 70% pure, more preferably about 80% pure, more preferably about 90% pure, more preferably about 95% pure, or substantially pure.

In another aspect, the present invention provides a method of purifying a protein, polypeptide or other substance which has the ability to modulate the activity of the HCV NS2/3 protease, the method including contacting the protein, polypeptide or other substance with an HCV NS2/3 protease polypeptide of the present invention.

A mixture of material including a protein, polypeptide or other substance which has the ability to modulate the activity of the HCV NS2/3 protease may be contacted against immobilised an HCV NS2/3 protease polypeptide of the present invention (e.g. immobilised either covalently or non-covalently such as via a specific binding molecule such as streptavidin or biotin) and molecules which do not bind to the polypeptide are washed off.

The protein, polypeptide or other substance which has the ability to modulate the activity of the HCV NS2/3 protease, in a purification method of the present invention, may be in a f mixture of molecules, such as a cellular extract, such as a normal cell of an organism such as a human or a recombinant host cell expressing the protein or polypeptide or its unphosphorylated form from encoding DNA, such as a bacterial, eukaryotic (e.g. mammalian or yeast) or insect cell, such as in a baculovirus expression system.

Following purification, the protein, polypeptide or other substance which has the ability to modulate the activity of the HCV NS2/3 protease may be used as desired, e.g. in a therapeutic context.

FIG. 1 shows a scheme for a high throughput screening assay for the NS2/3 protease inhibitors. In step 1, NS2/3 is refolded. The precursor is then activated in an appropriate buffer so that cleavage occurs (step 2). Uncleaved precursor is then captured (step 4) and the amount of free NS3 in solution measured (step 5).

Figure 2:
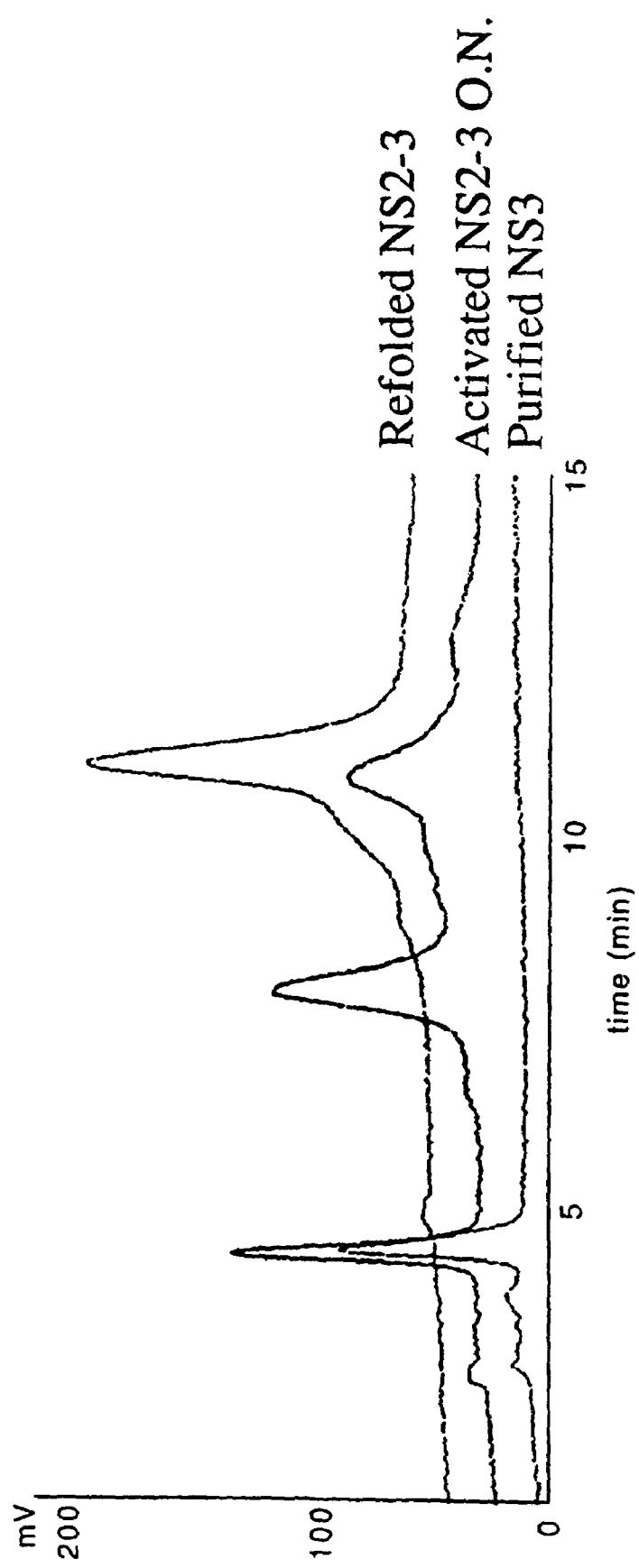

FIG. 2 shows the cleavage reaction products of NS2/3 seperated by HPLC, as follows. A solution of 5 µM $H_{6-907-1206}$-ASK4 protease in 6 M guanidine hydrochloride, 25 mM Tris pH 8.7, 100 mM DTT were diluted 50-fold into a buffer containing 50 mM Tris pH 7.5, 3 mM DTT, 50% glycerol, 1% CHAPS, 50 µM $ZnCl_2$, 250 mM NaCl at a temperature of 4° C. After 5 minutes the temperature was raised to 23° C. thereby initiating the cleavage reaction. Samples were analysed on a Poros R1/H perfusion chromatography column (4.6 mm×50 mm) equilibrated with 90% H20/0.1% TFA (buffer A) and 10% acetonitrile/0.08% TFA (buffer B). The column was operated at a flow rate of 2.5 ml/min using a Merck-Hitachi high performance liquid chromatograph equipped with a fluorescence detector. A gradient from 10%–90% B in 15 minutes was used to separate the precursor from its cleavage fragments. Protein peaks were detected by monitoring of tryptophan fluorescence (excitation 280 nm, emission 350 nm) and quantified by peak integration. Top gradient is refolded NS2/3, middle gradient is activated NS2/3 O.N. and bottom gradient is purified NS3.

Figure 3:
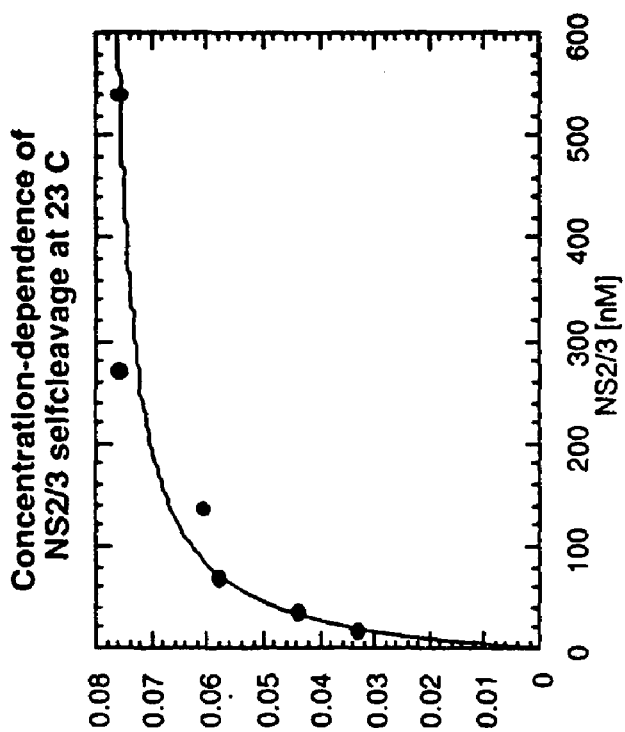
Figure 3:
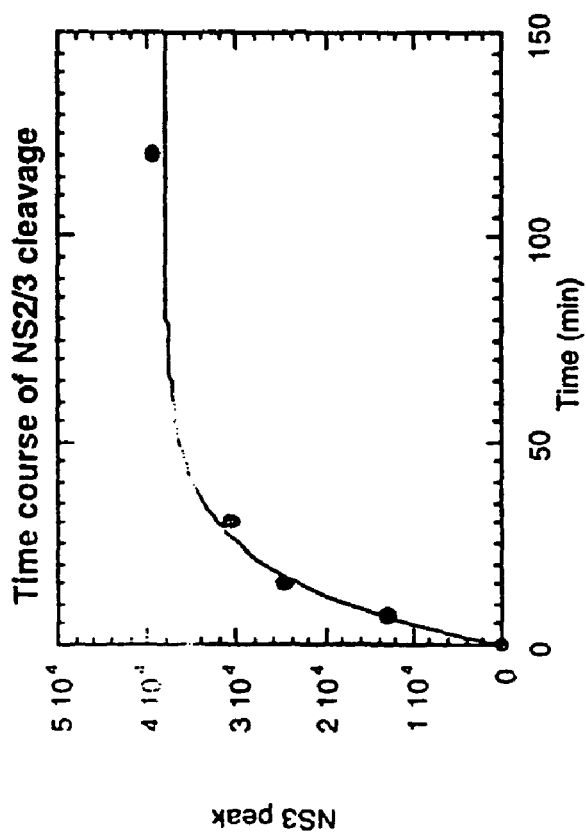

FIG. 3 shows an analysis of the cleavage reaction of 300 nM $H_6$-907-1206-ASK4 protease by HPLC. Left panel: analysis of the time course of the NS2/3 cleavage reaction. The area of the HPLC peak corresponding to the NS3 cleavage product was determined by peak integration and plotted as a function of incubation time. Data could be fitted with a single exponential equation to derive a value for the observed first order rate contant of the reaction. Right panel: Concentration dependence of NS2/3 self cleavage at 23° C. The first order rate constants of the cleavage reaction were determined as a function of protein concentration.

Figure 4:
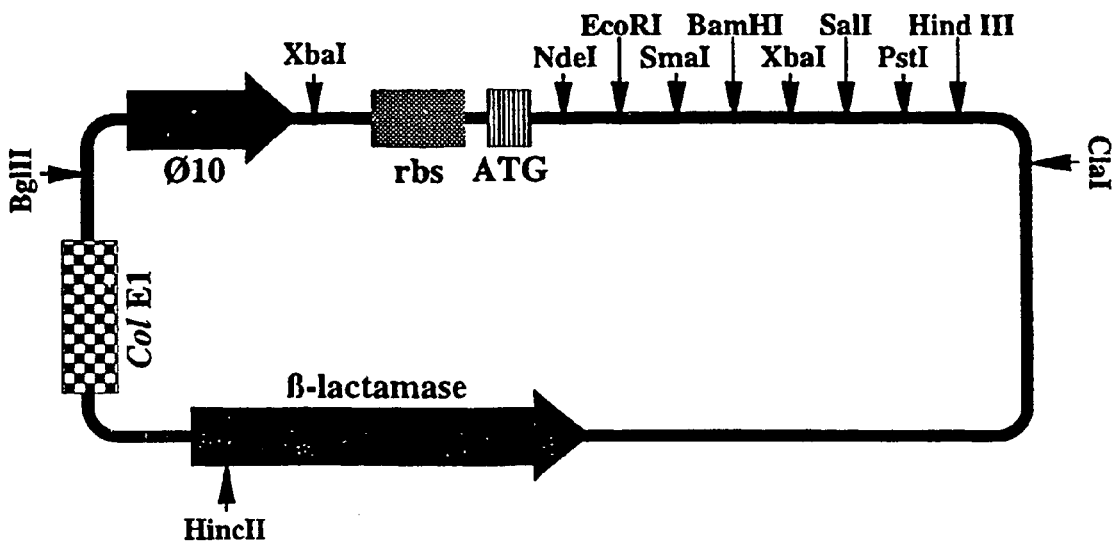
Figure 4:
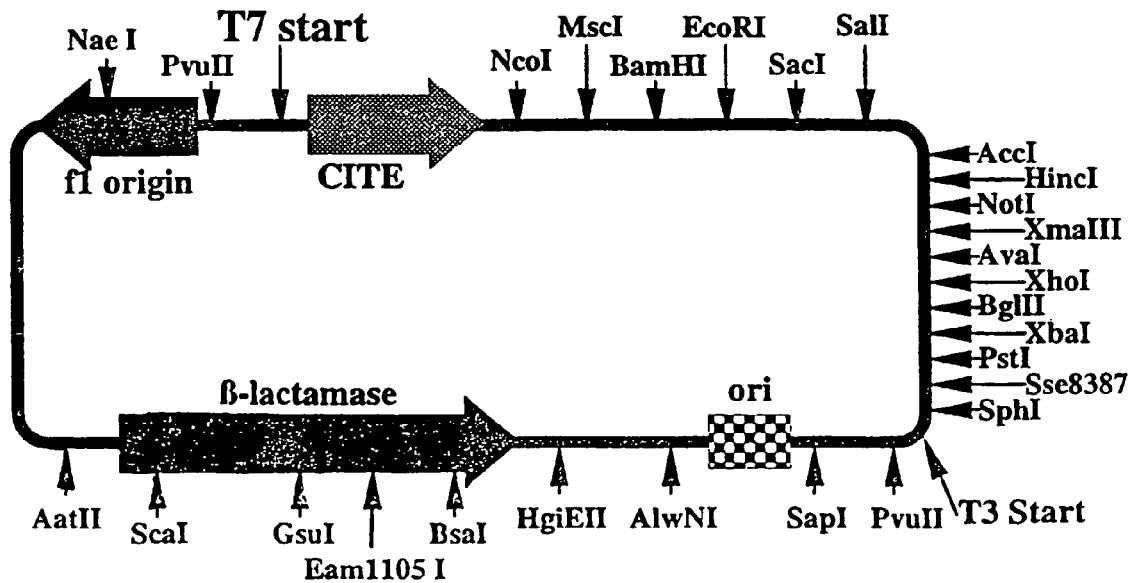

FIG. 4 shows a diagram of two expression plasmid vectors, pT7.7 (upper plasmid) and pCITE 2b (+) (lower plasmid) used for the cloning of fragments of cDNA encoding for the NS2/3 region of the HCV polyprotein.

EXPERIMENTAL

EXAMPLE 1

Subcloning of the NS2/3 Protease in Expression Vectors

PCR Amplification of NS2–3 Constructs

Plasmids suitable for the heterologous expression of active, wild type, or inactive mutants of NS2/3 have been generated by cloning of PCR-amplified fragments of cDNA encoding for the NS2/3 region of the HCV polyprotein into appropriate restriction sites.

Several expression plasmids are known in the art, both for eukaryotic and prokaryotic heterologous expression of proteins. In the present example the backbone of the pT7.7 vector is used for heterologous expression in prokaryotic (*E. coli*) cells, while pCITE 2b (+) is used for heterologous expression in eukaryotic cells (Hep 3b) or in vitro transcription/translation system. In principle other expression systems could be used to the same purpose.

cDNAs encoding the non-structural region of isolates corresponding to HCV strains J or H were used as templates for PCR amplification (HCV J strain, Genbank Acc. No. D90208; HCV H strain, Genbank Acc. No. M67463; HCV H77 strain, Genbank Acc. AF009606). DNA was routinely amplified by preparing an amplification reaction mixture composed of 20 U/ml Taq DNA polymerase mix in 60 mM $Tris-SO_4$ (pH 9.1 at 25 C), 18 mM $(NH_4)_2SO_4$, 2 mM $MgSO_4$, 200 µM dGTP, 200 µM dATP, 200 µM dCTP, 200 µM dTTP and stabilisers (PCR SuperMix High Fidelity, GibcoBRL, Cat. No.: 10790-020), called PCR protocol 1 in the following examples.

Alternatively, DNA was amplified by preparing an amplification reaction mixture composed of 10 mM Tris-HCl, 1.5 mM MgCl2, 50 mM KCl, pH 8.3 (20 C), 200 µM dGTP, 200 µM dATP, 200 µM dCTP, 200 µM dTTP and 2.5 U of Taq DNA Polymerase (Taq DNA Polymerase, Boehringer Mannheim, Cat. No.: 1146 173), called PCR protocol 2 in the following examples.

In some cases, a different amplification reaction mixture was used, composed of 10 mM Tris-HCl, pH 8.3, 50 mM KCl, 1.5 mM MgCl2, 0.001% gelatin, 200 µM dGTP, 200µM DATP, 200 µM dCTP, 200 µM dTTP and 2.5 U of AmpliTaq Gold(tm) (Perkin Elmer, Cat. No.: N808-0241), called PCR method 3 in the following examples.

In all cases, the reaction volume was 25 µl, specific primers were 200–500 nM each (final concentration) and template DNA was routinely between 20 and 100 ng (total amount per reaction). Reactions were assembled on ice, mixed thoroughly and loaded on the thermocycler at 95° C. PCR amplification was performed for 20–30 cycles of 95° C., 60 seconds. Annealing was generally performed for 15 seconds at a temperature 5° C. lower than the lowest melting temperature (Tm value) of the primers. Methods to calculate Tm values from the oligonucleotide sequence are known in the art and can be found in Sambrook et al. (1989). Molecular cloning, a laboratory manual. Cold Spring Harbor Laboratory Press.

Extension was performed at 72° C. (Taq DNA Polymerase, Boehringer Mannheim) or 68° C. (PCR SuperMix High Fidelity, GibcoBRL) for 60 second/Kb target length.

All PCR reactions were preceded by a single 1–2 minutes denaturation cycle performed at 95° C. (or 7 minutes for reactions performed with Taq Gold) and were terminated by a quick ramp to 4° C., alternatively the ramp to 4° C. was preceded by a single cycle performed at 72° C. for 7 minutes (see below for specific conditions). The thermocycler was from Perkin Elmer (GeneAMP PCR System 9700).

Following is a list of the oligonucleotide primers used for amplification:

|   | Primer Name | Sequence (5' to 3') |
|---|---|---|
| 1 | H NS3 Rev ASK4 | ttggaattcctacttcttcttcttgctagctc tcatggttgtctctaggttctc (SEQ ID NO: 1) |
| 2 | J NS2 Forw H6 | ggccacccaccaccaccaccaccacatggacc gagagatggctgcatcg (SEQ ID NO: 2) |
| 3 | J NS3 Rev ASK4 bis | ctacttcttcttcttgctagcccgcatggtag tttccatagactc (SEQ ID NO: 3) |
| 4 | J NS2 Forw | accgagagatggctgcatcgtgcgg (SEQ ID NO: 4) |
| 5 | J NS2 (903) Forw | caggctggcatgactagagtgccg (SEQ ID NO: 5) |
| 6 | J NS2 (907) Forw | actagagtgccgtactttgtacgc (SEQ ID NO: 6) |
| 7 | J NS2 (913) Forw | tacgcgctcagggctcatccgtgc (SEQ ID NO: 7) |
| 8 | J NS2 (919) Forw | atccgtgcatgcatgttagtgcgg (SEQ ID NO: 8) |
| 9 | J NS2 (919) H6 Forw | caccaccaccaccacacatccgtgcatgcat gttagtgcgg (SEQ ID NO: 9) |
| 10 | J NS2 Rev | ctaaaggagccgccaccctgtagacc (SEQ ID NO: 10) |
| 11 | J NS3 Rev | ctaccgcatggtagtttccatagactc (SEQ ID NO: 11) |
| 12 | J 903 pT7H6 | tgcatcatcatcatcatcatcaggctggcatg actagagtgccg (SEQ ID NO: 12) |
| 13 | J 903 pT7 | tgcaggctggcatgactagagtgccg (SEQ ID NO: 13) |
| 14 | J 907 pT7H6 | tgcatcatcatcatcatcatactagagtgccg tgtacgc (SEQ ID NO: 14) |
| 15 | J 907 pT7 | tgactagagtgccgtactttgtacgc (SEQ ID NO: 15) |
| 16 | H NS2 Forw H6 | ccacccaccaccaccaccaccctggacacg gaggtggccgcgtcg (SEQ ID NO: 16) |

Mutagenesis

Mutations were generally introduced by PCR-amplification of cDNA sequences using mutagenic primers. This method is well known to those skilled in the art and is described in: Sambrook et al. (1989), Molecular cloning, a laboratory manual. Cold Spring Harbor Laboratory Press, Ehrlich, H. A., (1989) PCR Technology Stockton Press, New York. and Zhao et al. (1993) Methods in Enzymology 217, 218. The PCR conditions were those described above.

Mutations can also be introduced using the U.S.E. (Unique Site Elimination) method of Deng, W. P. and Nickoloff, J. A., (1992) Anal. Biochem. 200, 81, with the U.S.E. Mutagenesis kit (Pharmacia Biotech, Cat. No.: 27-1699-01) or by restriction enzyme-subcloning of fragments containing the desired mutation(s).

Following is a list of the primers used for mutagenesis:

|   | Primer Name | Sequence (5' to 3') |
|---|---|---|
| 17 | H77 Forw (A1027P) | aggttgctgccgcccatcacggcg (SEQ ID NO: 17) |
| 18 | H77 Rev (A1027P) | cgccgtgatgggcggcagcaacct (SEQ ID NO: 18) |
| 19 | H77 Forw (H952A) | gtgtataacgctctcaccctctgc (SEQ ID NO: 19) |
| 20 | H77 Rev (H952A) | gcagaggggtgagagcgttatacac (SEQ ID NO: 20) |
| 21 | J (H952A) Forw Bis | acgtacgtatatgacgctcttactc cactgcgg (SEQ ID NO: 21) |
| 22 | J (H952A) Rev Bis | ccgcagtggagtaagagcgtcatat acgtacgt (SEQ ID NO: 22) |
| 23 | J Forw (A1027P) | cggctccttccgcctatcacggcc (SEQ ID NO: 23) |
| 24 | J Rev (A1027P) | ggccgtgataggcggaaggagccg (SEQ ID NO: 24) |
| 25 | J (C993A) Forw Not I/Eag I | gcagacaccgcggccgctggggaca tcatc (SEQ ID NO: 25) |
| 26 | J (NdeI-) Forw | ggctcatctggtggttacaatattt tatcaccagagccg (SEQ ID NO: 26) |
| 27 | U.S.E. Selection Primer Sca I/Mlu I | ctgtgactggtgacccgtcaaccaa gtc (SEQ ID NO: 27) |

Subcloning of NS2-3 in pT7.7 pT7.7 was the vector of choice in preparing constructs to be used for heterologous protein expression in prokaryotes (Studier, F. W., Rosenberg, A. H., Dunn, J. J. & Dubendorff, J. W. 1989. Methods in Enzymology 185, 60) CsCl$_2$ quality DNA (prepared according to Sambrook et al 1989: Ref above) was restricted with Nde I (Boehringer Mannheim) for 3 hrs at 37° C. and filled-in with Klenow DNA Polymerase (Boehringer Mannheim) following manufacturer instructions, i.e. by adding 33 μM of NTP and 1 U of enzyme/μg of plasmid for fifteen minutes at 25° C. The filled-in plasmid was loaded on a 1% TAE agarose gel, stained with 5 μg/ml ethidium bromide and electrophoresed.

After electrophoresis, the band corresponding to plasmid DNA was excised and gel purified with the Quiaex II kit (Quiagen, Cat No.: 20021). Following elution, the plasmid was dephosphorylated with Calf Intestinal Alkaline Phosphatase (Boehringer Mannheim) following manufacturer instructions and solution purified with the Quiaex II kit (Quiagen, Cat No.: 20021).

Inserts derived from PCR protocol 1 were phosphorylated directly in the PCR mix by addition of 5 mM ATP and 7.9U of T4 Polynucleotide Kinase (Pharmacia, Cat. No.: 27-0736-02) for 30 minutes at 37° C. Following phosphorylation, PCR products were loaded on a 1% TAE agarose gel, stained with 5 μg/ml ethidium bromide and electrophoresed. After electrophoresis the bands of interest were excised from the gel and eluted with the Quiaex II kit.

Ligations were performed by mixing the plasmid with the insert in a 1:3 molar ratio in a ligation mixture composed of 50 mM Tris-HCl (pH 8.7), 10 mM DTT, 1 mM ATP and 25 μg/ml bovine serum albumin with 400U of T4 DNA Ligase (New England Biolabs, Cat. No.: 202S) at 16° C. for at least 1 hour; alternatively the Rapid DNA Ligation kit was used following manufacturer instructions (Boehringer Mannheim, Cat. No.: 1635 379). Where possible mutations where shuttled from one construct to the other by restriction.

Following is a list of the constructs prepared in pT7.7 and used throughout these examples, [cloning site is Nde I for all pT7.7 constructs]:

| Const No | Name | PCR method | 5' primer | 3' primer | mutagenic primer |
|---|---|---|---|---|---|
| 1 | pT7-7 J H6-903-1206-K4 wt | 1 | 12 | 3 | / |
| 2 | pT7-7 J 903-1206 wt | 1 | 13 | 11 | / |
| 3 | pT7-7 J H6-907-1206-K4 wt | 1 | 14 | 3 | / |
| 4 | pT7-7 J H6-907-1206-K4 (H952A) | 1 | 14 | 3 | 21, 22 |
| 5 | pT7-7 JH6-907-1206-K4 (A1027P) | 1 | 14 | 3 | 23, 24 |
| 6 | pT7-7 JH6-907-1206-K4 (C993A) | 1 | 14 | 3 | 25, 27 |
| 7 | pT7-7 J 907-1206-K4 wt | 1 | 15 | 3 | / |
| 8 | pT7-7 J 907-1206-K4 (H952A) | 1 | 15 | 3 | 21, 22 |
| 9 | pT7-7 J 907-1206-K4 (C993A) | 1 | 15 | 3 | 25, 27 |
| 10 | pT7-7 J 907-1206-K4 (A1027P) | 1 | 15 | 3 | 23, 24 |
| 11 | pT7-7 J 907-1206 wt | 1 | 15 | 11 | / |
| 12 | pT7-7 J 907-1206 (H952A) | 1 | 15 | 11 | 21, 22 |
| 13 | pT7-7 J 907-1206 (A1027P) | 1 | 15 | 11 | 23, 24 |
| 14 | pT7-7 J H6-907-1026 wt | 1 | 14 | 11 | / |
| 15 | pT7-7 J 907-1026 wt | 1 | 15 | 11 | / |

Subcloning of NS2-3 in pCITE 2b (+)

pCITE 2b (+) (Novagen, Cat. No.: 69291-1) was the vector of choice for preparing constructs to be used for eukaryotic expression experiments or in vitro translation assays. $CsCl_2$ quality DNA was restricted with Nco I for 3 hrs at 37° C. and filled-in with Klenow DNA Polymerase following manufacturer instructions, i.e. by adding 33 μM of NTP and 1 U of enzyme/μg of plasmid for fifteen minutes at 25° C. The filled-in plasmid was loaded on a 1% TAE agarose gel, stained with 5 μg/ml ethidium bromide and electrophoresed. After electrophoresis the band corresponding to the plasmid DNA was excised and gel purified with the Quiaex II kit. Following elution, plasmid DNA was dephosphorylated with calf intestinal alkaline phosphatase following manufacturer instructions and solution purified.

Alternatively, the plasmid was restricted with MluN I and dephosphorylated following the protocol outlined above. In some other cases, pCITE 2b (+) was restricted with MluN I, EcoR I and dephosphorylated as above.

Inserts derived from PCR protocol 1 and 2 were phosphorylated directly in the PCR mix by addition of 5 mM ATP and 7.9 U of T4 Polynucleotide Kinase for 30 minutes at 37° C. Following phosphorylation, PCR products were loaded on a 1% TAE agarose gel, stained with 5 μg/ml ethidium bromide and electrophoresed.

After electrophoresis the band of interest was excised from the gel and eluted with the Quiaex II kit. When inserts were derived from PCR protocol 3, the cloning strategy implicated a first cloning step in PCRII.I (Invitrogen, Cat. No.: K2000-01), cloned fragments were then rescued by MluN I, EcoR I restriction and subcloned in pCITE 2b (+). When required by the cloning strategy, inserts prepared with PCR protocol 2 or 3 were polished with T4 DNA Polymerase (New England Biolabs, Cat. No.: 203S) according to manufacturer instructions and purified as outlined previously.

Ligations were performed by mixing the plasmid with the insert in a 1:3 molar ratio in a ligation mixture composed of 50 mM Tris-HCl (pH 8.7), 10 mM DTT, 1 mM ATP and 25 μg/ml bovine serum albumin with 400U of T4 DNA at 16° C. for at least 1 hour; alternatively the Rapid DNA Ligation kit was used following manufacturer instructions.

Where possible, mutations where shuttled from one construct to the other by restriction.

Following is a list of the constructs prepared in pCITE 2b (+):

| Cons No | Name | Cloning site | PCR Method | 5' primer | 3' primer | mutagenic primer |
|---|---|---|---|---|---|---|
| 16 | pCITE 2b (+) H H6-810-1206-K4 wt | MluN I EcoR I | 2, 3 | 16 | 1 | / |
| 17 | pCITE 2b (+) H H6-810-1206-K4 (H952A) | MluN I EcoR I | 2, 3 | 16 | 1 | 19, 20 |
| 18 | pCITE 2b (+) H H6-810-1206-K4 (A1027P) | MluN I EcoR I | 2, 3 | 16 | 1 | 17, 18 |
| 19 | pCITE 2b (+) J H6-811-1206-K4 wt | MluN I EcoR I | 2, 3 | 2 | 3 | / |

-continued

| Cons No | Name | Cloning site | PCR Method | 5' primer | 3' primer | mutagenic primer |
|---|---|---|---|---|---|---|
| 20 | pCITE 2b (+) J H6-811-1206-K4 (H952A) | MluN I EcoR I | 2, 3 | 2 | 3 | 19, 20 |
| 21 | pCITE 2b (+) J H6-811-1206-K4 (A1027P) | MluN I | 2, 3 | 2 | 3 | 17, 19 |
| 22 | pCITE 2b (+) J 810-1206 wt | MluN I | 1 | 4 | 11 | 26 |
| 23 | pCITE 2b (+) J 810-1206 (H952A) | MluN I | 1 | 4 | 11 | 19, 20, 26 |
| 24 | pCITE 2b (+) J 810-1206 (A1027P) | MluN I | 1 | 4 | 11 | 17, 18, 26 |
| 25 | pCITE 2b (+) J 903-1206 wt | Nco I | 1 | 5 | 11 | / |
| 26 | pCITE 2b (+) J 903-1206 (H952A) | Nco I | 1 | 5 | 11 | 19, 20 |
| 27 | pCITE 2b (+) J 903-1206 (A1027P) | Nco I | 1 | 5 | 11 | 17, 18 |
| 28 | pCITE 2b (+) J 907-1206 wt | Nco I | 1 | 6 | 11 | / |
| 29 | pCITE 2b (+) J 907-1206 (H952A) | Nco I | 1 | 6 | 11 | 19, 20 |
| 30 | pCITE 2b (+) J 907-1206 (A1027P) | Nco I | 1 | 6 | 11 | 17, 18 |
| 31 | pCITE2b (+) J 913-1206 wt | MluN I | 1 | 7 | 11 | / |
| 32 | pCITE 2b (+) J 919-1206 wt | Nco I | 1 | 8 | 11 | / |
| 33 | pCITE 2b (+) J H6-919-1206 wt | Nco I | 1 | 9 | 11 | / |
| 34 | pCITE 2b (+) J 810-1026 wt | MluN I | 1 | 4 | 11 | 26 |
| 35 | pCITE 2b (+) J 810-1026 (H952A) | MluN I | 1 | 4 | 11 | 19, 20, 26 |

Transformation of Competent Cells

For cloning purposes and DNA propagation all constructs were transformed in E. coli Top10 cells; transformation was accomplished according to the $CaCl_2$ method Sambrook et al (Sambrook, J., Fritsch E,. F., Maniatis, T., 1989, Molecular cloning, a laboratory manual. Cold Spring Harbor Laboratory Press.)

All deletion mutants were generated in the context of the HCV J-strain and then cloned into a pCITE vector and tested in a coupled in vitro transcription/translation system (see below). The deletion mutants starting at residues 903 and 907 showed full cleavage activity when compared with a wild-type construct, starting at residue 810, whereas NS2/3 913–1207 was inactive.

All constructs yielded high levels (>5 mg/l) of heterologous protein expression in E. coli. A high level of auto-processing, varying from 50 to 80%, was observed after 3 hours induction at 23° C.

EXAMPLE 2

Expression of NS2/3 Protease Constructs in in vitro Transcription/Translation Systems (IVT).

In vitro translation (IVT) assays were performed with the Rabbit Reticulocyte Lysate System or with the TnT T7 Quick Coupled Transcription/Translation System (Promega, Cat. No.: L4151 and L1170) following manufacturer instructions.

DNA suitable for IVT was prepared by $CsCl_2$ or with the Wizard Plus SV DNA Purification System (Promega, Cat. No.: A1460). DNA was generally linearized with the appropriate restriction enzyme for 3 hrs and precipitated with $CH_3COONa/EtOh$. In some cases, DNA was phenol extracted from solution before EtOh precipitation. Precipitated DNA was then resuspended in water and a small aliquot loaded on a 1% TAE agarose gel stained with ethidium bromide, to check restriction and concentration. Linear DNA was used as a template for in vitro T7 RNA polymerase-driven transcription (Stratagene, Cat. No.: 600124).

Transcribed RNA was phenol extracted and precipitated with $CH_3COONa/EtOh$. RNA was then separated from template DNA by centrifugation through a G-50 spin column (Pharmacia, Cat. No.:17-0043-01) (Sambrook, J., Fritsch E,. F., Maniatis, T., (1989). Molecular cloning, a laboratory manual. Cold Spring Harbor Laboratory Press.) Purified RNA was precipitated as above and resuspended in water.

RNA was routinely translated by preparing a reaction mixture composed of 30 mM $CH_3COOK$, 360 µM $MgCl_2$, 30 µM amino acid mix minus methionine, 1µg of RNA, reticulocyte lysate 10 µl, 90 mM DTT, radioactively labelled methionine 2 µl (Amersham, Cat. No.:SJQ0079), RNasin (Promega, Cat. No.: N2511) 1 µl and water to 33 µl. The TnT system was used with linear DNA in a reaction mixture composed of 10 µl of TnT reticulocyte lysate, 30 mM $CH_3COOK$, 360 µM $MgCl_2$, 30 µM aminoacid mix minus methionine, 1 µg of DNA, 21 mM DTT, radioactively labelled methionine 2 µl, RNasin 1 µl and water to 33 µl.

Radiolabelled proteins were separated on SDS-page. (Sambrook, J., Fritsch E, F., Maniatis, T., (1989). Molecular cloning, a laboratory manual. Cold Spring Harbor Laboratory Press). Gels were fixed in destaining solution for 30 minutes, followed by 30 minutes soaking in Amplify (Amersham, Cat. No.: NAMP 100) under gentle shaking, dried on 3 MM paper and subjected to autoradiography.

Using the IVT methodology, N-terminally truncated versions of NS2/3 from the HCV J-strain starting with amino acids 903, 907, 913 and 919 all ending at amino acid 1206 (Construct numbers 25, 28, 31 and 33 from Example 1) were compared in IVT to the construct number 19, having the native N-terminus.

An autoradiogram of labelled products expressed from NS2/3 constructs was obtained. The autoradiogram was prepared as follows; NS2/3 constructs were produced by in vitro translation in the presence of $^{35}$S labelled methionine using the TnT T7 Quick Coupled Transcription/Translation System. After 1 hour incubation at 23 C reactions were stopped by the addition of SDS sample buffer and analysed by SDS 12.5% PAGE. Gels were soaked with Amplify™ and analysed by autoradiography.

The experiment showed that N-terminal deletions up to residue 907 are tolerated without impairment of the catalytic activity of the NS2/3 protease. The truncated constructs offer the advantage that they are devoid of a large hydrophobic N-terminal portion that could cause aggregation of the protein during heterologous expression.

EXAMPLE 3

Transient Expression of NS2/3 Protease Construct in Eukaryotic Cells.

The activity of the HCV NS2/3 protease and its inhibition was investigated using transient expression in eukaryotic cells.

Hep3B or HeLa cells are well suited for this purpose. HeLa cells are seeded at a density of $6 \times 10^5$ cells/plate and infected with vaccinia virus vTF7-3 at a multiplicity of 5 PFU per cell. This infection will lead to the expression of T7 RNA polymerase in the cells and can be used to express proteins under the control of a T7 RNA polymerase promoter. The method is extensively described in Tomei et al, (1993) J. Virol. 67, 4017 and Kohara et al, (1992) J. Gen. Vir. 73: 2313–2318.

After adsorption for 30 minutes at 37° C., 3 ml of Dulbecco's modified Eagle's MEM supplemented with 10% fetal calf serum were added. Cells were incubated for an additional 30 minutes at 37° C. 20 µg of recombinant plasmid containing NS2/3 protease constructs according to construct numbers 16–35 are precipitated in calcium phosphate as described in Sambrook et al (1989), and added directly to each plate in a 500 µl volume.

At 4 hours post-transfection the medium was replaced with MEM lacking methionine (Gibco Cat No.: 31900-020) and the cells were starved for 1 hour at 37° C. Cells were then radiolabelled for 3 hours with 400 µCi of Tran$^{35}$S label (ICN Cat No.:51006) in 2 ml MEM lacking methionine and supplemented with 2% dialyzed fetal calf serum. Cells were harvested and resuspended in 20 mM Tris pH 8.0, 150 mM NaCl, 1% Triton X-100, 1 mM phenylmethylsulfonyl fluoride, 1 mM EDTA and 1 mM dithiothreitol.

NS2/3 protease expression and activity can be determined in cell extracts upon immunoprecipitation with specific antisera. To this purpose, sodium dodecyl sulphate and dithiothreitol are added to the cell extract to final concentrations of 2% and 10 mM, respectively. The lysates were then incubated at room temperature for 1 hour and heated to 95° C. for 10 minutes. 10 µl of antisera were pre-adsorbed for 1 hour at 4° C. in a 400 µl volume of 20 mM Tris pH 8.0, 150 mM NaCl, 1% Triton X-100 with vT7F3-infected HeLa cell extracts spotted on nitrocellulose filters.

The antibody suspension was then incubated with 60 µl of protein A Sepharose for 1 hour at 4° C. The resin was pelleted by centrifugation, washed three times in 20 mM Tris pH 8.0, 150 mM NaCl, 1% Triton X-100 and resuspended in 400 µl of the same buffer. 20 µl of cell lysate were added to the resin and incubated for 1 hour at 4° C.

The protein A sepharose suspension was subsequently layered on 0.9 ml of 5 mM Tris pH 7.4, 16.5 mM EDTA, 0.1% sodium deoxycholate, 0.25% Nonidet P-40, 30% (w/v) sucrose and pelleted by centrifugation in a microcentrifuge at room temperature. The pellet was washed twice with the same buffer in the absence of sucrose and once with water. Samples were analysed by autoradiography upon separation by SDS-polyacrylamide electrophoresis.

EXAMPLE 4

Expression in *E. coli* in the Presence and Absence of Zn Ions.

Several systems for the heterologous expression of active NS2/3 protease are known in the art. In the present example *E. coli* was used for the expression of NS2/3 protease. These cells were also driven to express the NS2/3 protein in an uncleaved form according to procedure outlined below. Other bacterial or eukaryotic expression systems may be used for the same purpose.

pT7—7 vectors containing truncated NS2/3 protease sequences according to construct numbers 1–15 were used to transform *E. coli* BL21 (DE3). Cells were grown in M9 minimal medium supplemented with 50 µM biotin, 2.4 µg/ml thiamine, 3.4 µg/ml FeSO4 and 200 µM Zn Cl$_2$ at 37° C. to an optical density at 500 nm of 0.8. Temperature was decreased to 23° C. and protein induction was initiated by the addition of 200 µl IPTG. After 3 hours, cells were harvested by centrifugation.

Cell extracts may be analysed by polyacrylamide gel electrophoresis run under denaturing conditions. This experiment provided evidence for the efficient induction of NS2/3 precursor protein in addition to two proteins migrating with the apparent molecular weights of the expected NS3 and NS2 cleavage products.

Since the NS2/3 precursor undergoes substantial self-processing during its induction, it is clearly not possible to obtain large amounts of pure, uncleaved precursor protein under these conditions. Two strategies were therefore attempted to decrease or halt the self processing reaction during protein induction.

1. Induction at Low Temperature.

Induction at 15° C. decreased the total amount of protein produced but only slightly affected the relative extent of self-processing. A further decrease of temperature leads to a severe impairment of protein production. It therefore appeared that the relative amount of potentially purifiable precursor cannot be increased through the modulation of temperature during induction.

2. Induction in Minimal Medium with Low Zinc Content.

The NS3 protein is known to contain stoichiometric amounts of zionc which are required for its folding and stability (De Francesco et al, 1996). If the NS3 protein is induced in *E. coli* grown in minimal medium in the absence of added zinc, it will not fold properly and forms aggregates known as inclusion bodies. The truncated NS2/3 protease constructs will drive the formation of insoluble protein if expressed in *E. coli* grown in M9 minimal medium not supplemented with zinc ions. Under these conditions, most of the NS2/3 protein is found as an uncleaved precursor and only very low amounts of NS3 cleavage product are visible on a Coomassie-stained gel. This procedure therefore provides a way of expressing the NS2/3 protease in a latent, uncleaved form.

In summary, to obtain a catalytically competent NS2/3 precursor in a latent, inactive form which is potentially amenable for purification, induction of the protein was performed in minimal growth medium in the absence of zinc.

EXAMPLE 5

Purification of the Unprocessed NS2/3 Protease from Inclusion Bodies.

To obtain NS2/3 protease in a pure form from bacterial cells, E. coli cells were grown in minimal medium in the absence of added zinc ions and were induced to produce NS2/3 proteins using construct numbers 1–15 (see Example 1), as outlined above.

The cells were harvested by centrifugation and the cell pellet was washed with PBS buffer (25 mM sodium phosphate pH 7.5, 140 mM NaCl). The washed pellet was next resuspended in lysis buffer (40 ml/l of growth medium) containing 25 mM sodium phosphate pH 6.5, 3 mM DTT, 500 mM NaCl, 0.5% CHAPS and 15% glycerol. Upon disruption of bacterial cell walls using a French pressure cell, 10 mM $MgCl_2$ was added to the homogenate which was then incubated for 30 minutes at 4° C. in the presence of 6 U/μl DNase. The homogenate was centrifuged for 15 minutes at 12000×g.

The pellet of the centrifugation contained the NS2/3 protein in addition to other bacterial protein contaminants. It was washed twice with lysis buffer, once with lysis buffer supplemented with 1% NP-40 and once with 20 mM sodium phosphate pH 7.5, 3 mM DTT. The final pellet typically contained an 80% pure NS2/3 protein.

The protein may be further purified using the following procedure. The pellet was resuspended in 7 M guanidine hydrochloride, 25 mM Tris pH8.7, 100 mM DTT and loaded on a 26/60 Superdex 75 gel filtration column (Pharmacia) equilibrated with 6 M guanidine hydrochloride, 25 mM Tris pH 7.5, 3 mM DTT, 150 mM NaCl and operating at a flow rate of 2 ml/min. The fractions containing NS2/3 are pooled and loaded on a 0.5×20 cm Source 15RPC reversed phase chromatography column (Pharmacia) equilibrated in 90% H20, 0.1% TFA (solvent A) and 10% acetonitrile 0.08% TFA (solvent B).

A gradient from 10% B to 90% B in 1 hour at a flow rate of 4 ml/min was used to elute the NS2/3 protein in a pure form from the column. The NS2/3 containing fractions were pooled, lyophilized and the protein was resolubilized in 7 M guanidine hydrochloride, 25 mM Tris pH 8.7, 100 mM DTT.

Typically, the protein had a purity >95% and was obtained with a yield >2 mg/l of bacterial culture. The purified protein was characterized by electrospray mass spectrometry, thereby verifying that no modifications of the protein took place during the expression or purification procedure.

The mass found by this technique for NS2/3 H6-907-1206-ASK4 was 33694 Da and corresponded to its theoretical mass calculated from the amino acid composition. This documents that no detectable modification of the proteins had occurred during this purification procedure. This notion is further corroborated by N-terminal amino acid sequence analysis done using Edman degradation on a gas-phase sequencer. This analysis gave the expected N-terminal sequence M-H-H-H (SEQ ID NO: 28).

The yields of pure protein that were obtained varied considerably among the different constructs 1–15 listed in Example 1. The highest levels of bacterial protein expression were obtained with the His+Lys tagged constructs using E. coli BL-21 cells. The expression of the NS2/3 907–1206 $ASK_4$-based mutant constructs was very low and had to be optimised. For these constructs, the highest levels of expression were obtained using E. coli B834 cells and minimal medium.

EXAMPLE 6

Refolding of the Purified NS2/3 Protease

A systematic screen for re-folding conditions was set up, varying the following parameters: re-folding methodology (dialysis, rapid dilution, stepwise dilution), protein concentration (10–100 μg/ml), pH (6–9), ionic strength (25–275 mM), polar additives (0.5 M arginine), non-polar additives (20% glycerol, 1% sucrose), residual chaotrope concentration (0–0.75 M guanidine), detergent (2% CHAPS), PEG 4000 (0.05%), temperature (4–23° C.) and $Zn^{++}$ concentration (30–100 μM). In all of the experiments, the recovery of soluble precursor upon ultracentrifugation was monitored.

Using this methodology, the following factors were identified as being important for the recovery of soluble protein after refolding: removal of chaotrope by dialysis, protein concentration <100 μg/ml, residual chaotrope concentration of 0.75 M guanidine in the refolding buffer, ionic strength >200 mM NaCl. Under suitable refolding conditions, more than 80% of the refolded precursor may be found in the supernatant after 120K ×g ultracentrifugation.

From this two methods were developed that can be used for different purposes. Method A allows to generate a refolded protein at micromolar concentrations that does not undergo cleavage unless transferred into an appropriate buffer, capable of sustaining the cleavage reaction. Method B allows the refolding of unfolded NS2/3 protein in a buffer that simultaneously sustains the cleavage reaction.

Method A. 200 μl of a solution containing 3 μM NS2/3 protease polypeptide in 6 M guanidine hydrochloride, 25 mM Tris pH 8.7, 100 mM DTT are dialysed against 20 ml of 50 mM Tris pH 7.5, 50 μM Zn Cl2, 3 mM DTT, 250 mM NaCl, 750 mM guanidine hydrochloride using a SpectraPor dialysis membrane with a cut-off of 10 kDa. The dialysis is performed at 4° C. After two hours the protein solution can be withdrawn, aliquoted and shock-frozen in liquid nitrogen. No cleavage occurs during this dialysis and the protein can be activated to undergo cleavage upon addition to a buffer that activates the cleavage reaction as outlined below.

Method B. A solution of 5 μM NS2/3 protease polypeptide in 6 M guanidine hydrochloride, 25 mM Tris pH 8.7, 100 mM DTT is diluted 50-fold into a buffer containing 50 mM Tris pH 7.5, 3 mM DTT, 50% glycerol, 1% CHAPS, 50 μM ZnCl2, 250 mM NaCl at a temperature of 4° C. After 5 minutes the temperature is raised to 23° C. thereby initiating the cleavage reaction.

For both methods A and B, variations of the composition of the buffers and of the protein concentration are possible and their consequences are outlined in more detail below. The yield of refolded, active protein varies between 30% and 80% and depends on the buffer composition, the amino acid composition of the NS2/3 protein and its purity.

EXAMPLE 7

Detecting the in Vitro Activity of the Purified NS2/3 Protease

Proteins refolded according to method A were diluted at least 5-fold into a buffer having the following composition (activity buffer): 50 mM Tris pH 7.5, 3 mM DTT, 50% glycerol, 1% CHAPS, 50 µM ZnCl2, 250 mM NaCl.

At timed intervals, aliquots of the activity buffer containing refolded NS2/3 protease were withdrawn, the reaction was stopped by addition of 0.1% sodium dodecyl sulfate and samples were loaded on a 12.5% sodium dodecyl polyacrylamide gel and analysed upon electrophoresis by silver stain or by Western blot.

Proteins refolded according to Method B were simply incubated at 23° C. for up to two hours and analysed in the same way.

After two hours of incubation under these conditions, an intense band, migrating with the molecular weight of truncated NS3 was detected on Western blots stained with anti NS3 antibodies.

On silver stained SDS-PAGE two bands corresponding to the Mw of the truncated NS2 and NS3 proteins were detected in addition to the uncleaved precursor. About 30% of the precursor protein was estimated to have been processed in this experiment.

A more convenient and quantitative format of an NS2/3 protease assay involves the separation of precursor and products by HPLC. The following method was developed: Proteins refolded according to method A or B were incubated in activity buffer at 23° C. At timed intervals 200 µl-aliquots were withdrawn and 20 µl 10% TFA were added to stop the reaction. The solution was injected on a Poros R1/H perfusion chromatography column (4.6 mm×50 mm, PerSeptive Biosystems, Cat No.: 1-1014-24) equilibrated with 90% H20/0.1% TFA (buffer A) and 10% acetonitrile/0.08% TFA (buffer B).

The column was operated at a flow rate of 2.5 ml/min using a Merck-Hitachi high performance liquid chromatograph equipped with a fluorescence detector. A gradient from 10%-90% B in 15 minutes was used to separate the precursor from its cleavage fragments. Using the monitoring of tryptophan fluorescence (excitation 280 nm, emission 350 nm) less than 5 nM protein can be reliably detected and quantified by peak integration.

FIG. 2 shows two typical chromatograms recorded at time zero and upon overnight incubation of NS2/3 H6-907-1206-ASK4 (Construct Number 3) in activity buffer. The peak marked "NS3" co-migrated with a protein standard encompassing amino acids 1027–1206 and carrying the C-terminal extension ASKKKK (SEQ ID NO: 29). To further verify that during the auto-cleavage reaction of purified NS2/3 protease processing occurred at the authentic cleavage site, the NS3 cleavage product was isolated and characterized using N-terminal sequence analysis by Edman degradation. The sequence obtained was A-P-I-T (SEQ ID NO: 29), that corresponds to residues 1027–1030 of the HCV polyprotein and unambiguously indicated that cleavage had occurred at the authentic NS2/3 site.

We estimated a first order rate constant of 0.06 min$^{-1}$ for the cleavage reaction and a t/2 of 11.5 minutes. These data are not dissimilar from published data on the cleavage reaction of full-length NS2/3 constructs in an in vitro transcription/translation system, in which t/2 of 10–15 minutes and a maximum cleavage of 70% were found.

Using several different enzyme preparations, we obtained between 15 and 80% of cleavage and rates of 0.03 min$^{-1}$–0.07 min$^{-1}$. The cleavage fragments were submitted for N-terminal sequence analysis to verify that cleavage occurred at the authentic cleavage site.

The NS3 protease activity of the refolded NS2/3 $H_6$907-1206-ASK$_4$ precursor was also investigated. No significant change in NS3 protease activity was noticed during an auto-cleavage reaction which led to 30% of processing after two hours of incubation. The extent of NS3 protease activity was compatible with the presence of about 25% of active-molecules, assuming that the specific activity of the NS3 protease is unchanged in the NS2/3 $H_6$907-1206-ASK$_4$ precursor.

These experiments show that the amount of catalytically competent protein that can be recovered has both NS2 and NS3 protease activities. The remainder of the protein is probably mis-folded.

EXAMPLE 8

Characterization of the Activity of the NS2/3 Protease

The HPLC method for detection of cleavage products arising upon incubation of the purified and refolded NS2/3 protease in activity buffer can be used to quantify the kinetic parameters of the reaction and to determine the influence of different physico-chemical conditions on its rate.

FIG. 3 shows a typical cleavage time course. 30 nM NS2/3 protease were incubated in 50 mM Tris pH 7.5, 3 mM DTT, 50% glycerol, 1% CHAPS, 50 µM ZnCl$_2$, 250 mM NaCl and the cleavage reaction was followed by measuring the amount of NS3 cleavage product formed with time. This was done by integrating the NS3 HPLC peak area.

In FIG. 3, left panel, a plot of NS3 peak area versus time is shown. The data points can be best fitted with a single exponential equation, allowing the assignment of an apparent rate constant. It was found that this rate constant is affected by the variation of several parameters such as ionic strength, glycerol concentration, pH, detergent concentration.

An unexpected finding is the fact that the rate constant also shows a protein-concentration dependency (FIG. 3, right panel). This is indicative of a multimer being the active species. In fact, gel filtration chromatography showed evidence for a dimeric species being formed in solution. Dimerization is a novel property of the NS2/3 protease that could be used to develop a strategy aimed at finding inhibitors of NS2/3 that interfere with dimer formation.

EXAMPLE 9

Assays for Inhibitors of the NS2/3 Protease

The invention also provides methodologies that can be used to identify inhibitors of the cleavage reaction. Such inhibitors can be found by screening compound collections or combinatorial libraries for NS2/3 protease inhibitory activity. Conveniently, small organic molecules are solubilized in DMSO and added to the assay. In all of the following assays the addition of up to 10% DMSO is tolerated without substantial impairment of NS2/3 protease cleavage activity.

The following methods are examples of assay methods that may be used:

A. Cell-Based Assay

Expression plasmids suitable for transient expression of NS2/3 protease in eukaryotic cells (pCITE construct numbers 16–35; Example 1) are described herein. These plasmids contain the NS2/3 protease under the control of a T7 RNA polymerase promotor. The use of this system to monitor expression of heterologous proteins in eukaryotic cells and—more specifically—to monitor the activity of viral proteases is well known in the art, (Tomei, L. et al. (1993). J. Virol. 67, 4017.) and described in Example 3.

Inhibition of NS2/3 protease activity by externally added molecules results in decreased levels of cleavage products that can be determined upon radiolabelling of proteins and isolation of NS2/3 protease and its NS3 cleavage product by immunoprecipitation with anti NS3 antisera, using established methods known in the art.

B. In Vitro Translation Assay

Active NS2/3 protease can be generated using a coupled in vitro transcription/translation system or by in vitro translation of the appropriate RNA molecules as outlined above (Example 2).

The invention provides plasmids suitable for T7 RNA polymerase driven production of NS2/3 protease encoding RNA molecules according to procedures known to those skilled in the art. Inhibitors are added to the reaction mixture and their potency determined by titration experiments.

Radiolabeling of proteins by addition of radioactively labelled amino acids and the subsequent analysis by SDS-PAGE and autoradiography allows monitoring of the inhibition of NS2/3 protease activity by a decrease in the amount of radioactive cleavage products.

C. Cleavage Detection by SDS Page or HPLC

NS2/3 protease constructs provided by this invention are purified and refolded according to the methods of this invention and incubated in 200 µl of activity buffer (50 mM Tris pH 7.5, 3 mM DTT, 50% glycerol, 1% CHAPS, 50 µM $ZnCl_2$, 250 mM NaCl) or another buffer suitable for sustaining the cleavage activity. Typically, 30 nM to 300 nM NS2/3 protease are used in the assay and incubated in the appropriate buffer in the absence or in the presence of up to 10% (v/v) of a solution of organic compounds in DMSO. At the lower the protein concentration the NS2/3 protease is present in the solution both as active dimer and as inactive monomer. This leads to a slower overall reaction rate.

The use of protein concentrations similar to or below the equilibrium dissociation constant of the dimer may be advantageous if one wishes to find inhibitors of dimer formation. Furthermore, low protein concentration may also be required to determine the activity of very potent inhibitors. At protein concentrations above 100 nM most of the protein will be present as active dimer and the cleavage reaction will be faster than at low protein concentration (see also FIG. 3).

Depending on the protein concentration used in the assay, the reaction is allowed to proceed for 10 to 30 minutes and stopped either by inactivating the NS2/3 protease through the addition of 20 µl 10% TFA (if the cleavage is detected by HPLC) or of SDS sample buffer (if cleavage is detected by SDS PAGE). In each case, the reaction is stopped in the linear range of the time course curve (FIG. 3). This is important since deviation from linearity may lead to an underestimation of the potency of added inhibitors.

Subsequently, the amount of cleavage product formed in the absence of inhibitor is compared to the amount of the same cleavage product formed in the presence of added inhibitor. The % inhibition is calculated from this comparison and determined at different inhibitor concentrations, leading to an accurate determination of the potency of the inhibitory compound. Either the generation of the NS3 or the NS2 cleavage fragment can be monitored to this end.

Using SDS PAGE as detection method, it is convenient to perform a Western blot stained with either NS2 or NS3-specific antisera to improve sensitivity. The intensity of the bands can be estimated by densitometry or other imaging techniques known in the art.

The preferable detection method is HPLC that allows the quantitative detection of uncleaved NS2/3 and both the NS2 and NS3 cleavage fragments within a few minutes. The assay can be used to screen collections of chemical compounds using robotic sample assembly and analysis. An example of an HPLC run documenting the separation and quantification of NS2/3, NS2 and NS3 is shown in FIG. 2.

D. High Throughput Screening Assay

Large compound collections or combinatorial libraries often containing >$10^5$ distinct chemical entities are promising sources for lead compounds in a drug development program. Handling of such large numbers of compounds requires robotic technologies and an assay that can be performed in a microplate format. The invention therefore also provides methods to assay NS2/3 protease activity in a microplate assay.

The assay, which is outlined in FIG. 1, was performed as follows: A six-histidine tag was engineered at the N-terminus of NS2/3 protease polypeptide. The tagged protein was purified as specified above and refolded following the refolding procedures A or B. For the sake of simplicity, refolding procedure B was preferred, whereby denatured, histidine tagged NS2/3 protease polypeptide was diluted into 100 µl activity buffer (50 mM Tris pH 7.5, 3 mM 2-mercaptoethanol, 50% glycerol, 1% CHAPS, 50 µM $ZnCl_2$, 250 mM NaCl) at a final concentration of 50 nM.

Incubation for 15 minutes at 23° C. results in partial processing of the NS2/3 protease. Incubation time was chosen in order to obtain about 10% of processing. Only the NS2 cleavage fragment and the uncleaved NS2/3 precursor possess histidine tags. These histidines may be captured by the addition of a metal affinity resin. Hence, after the incubation period 100 µl of a 50% (v/v) slurry of a Talon metal affinity resin (Clontech, Cat No.: 8901-3) equilibrated in 50 mM Tris pH 7.5, 250 mM NaCl were added. The resin sequestered the histidine-tagged species and left the untagged NS3 molecule in solution.

The NS3 molecule generated during the processing reaction of the NS2/3 protease has a serine protease activity. This activity may be used as readout of the processing reaction between NS2 and NS3. In fact, the catalytic activity of NS3 will amplify each NS2/3 processing event, e.g. through turnover of a fluorogenic NS3 substrate.

After sedimentation of the resin a 40 µl aliquot of the supernatant was withdrawn and added to a well of a second 96well microplate containing 200 µl 50 mM Tris pH 7.5, 0.1% Triton X-100, 10 mM DTT, 15% glycerol, 150 mM NaCl and 20 µM Pep4AK, having the sequence KKKGS-VVIVGRIILSGR-NH2 (SEQ ID NO: 31). Pep4AK is a co-factor of the NS3 protease and was added in order to obtain maximum activity.

At this point, 5 µM of an internally quenched fluorogenic NS3 substrate having the sequence Mca-DDIVPCSMSK (SEQ ID NO: 32) was added. The reaction was followed using a fluorescence microplate reader (excitation 325 nm, emission 393 nm)

Robotic handling of all the steps required for this assay is possible, allowing screening of a large number of compounds in a short time period. Furthermore false positives that could arise due to inhibition of the NS3 protease are minimized due to the tenfold dilution of the original solution during the NS3 protease assay.

The invention claimed is:

1. An isolated polypeptide consisting of a fragment of a native HCV NS2/3 protease precursor, wherein the amino terminus of the fragment is at a position corresponding to a position between positions 903 to 913 in the HCV NS2/3 protease precursor amino acid sequence set forth in SEQ ID NO:34 and the carboxyl terminus of the fragment is at a position corresponding to a position between positions 1206 to 1657 in the HCV NS2/3 protease precursor amino acid sequence set forth in SEQ ID NO:34, which polypeptide when in a homodimer has auto-proteolytic activity.

2. A polypeptide according to claim 1 wherein the C-terminal residue of the fragment is the amino acid that is at position 1206 in the HCV NS2/3 protease precursor.

3. A polypeptide according to claim 2 wherein the N-terminal residue of the fragment is the amino acid that is at position 903 in the HCV NS2/3 protease precursor.

4. A polypeptide according to claim 2 wherein the N-terminal residue of the fragment is the amino acid that is at position 907 in the HCV NS2/3 protease precursor.

5. An isolated polypeptide consisting of an amino acid sequence that has 95% sequence identity over its length compared with a fragment of a native HCV NS2/3 protease precursor, wherein the amino terminus of the fragment is at a position between positions 903 to 913 in the HCV NS2/3 protease precursor amino acid sequence and the carboxyl terminus of the fragment is at a position between positions 1206 to 1657 in the HCV NS2/3 protease precursor amino acid sequence, which polypeptide when in a homodimer has auto-proteolytic activity, and wherein the HCV NS2/3 protease precursor is encoded by a nucleic acid sequence encoding the HCV polyprotein of the HCV H strain set forth in SEQ ID NO: 34.

6. A polypeptide comprising the fragment of a native HCV NS2/3 protease precursor according to claim 1, and further comprising a fusion of one or more heterologous amino acid residues at either or both of its amino or carboxyl termini.

7. An assay method for testing the ability of an agent to inhibit the auto-proteolytic activity of an HCV NS2/3 protease, comprising:
(a) bringing a test agent into contact with a polypeptide according to claim 1 or a homodimer of two said polypeptides; and
(b) measuring at least one of either:
(i) homodimer formation of two said polypeptides as an indication of the ability of the agent to inhibit HCV NS2/3 protease activity, wherein in the absence of said agent homodimer formation occurs, or
(ii) HCV NS2/3 protease auto-proteolytic activity as an indication of the ability of the agent to inhibit HCV NS2/3 protease activity, wherein in the absence of said agent NS2/3 protease activity is retained,
thereby determining the ability of the agent to inhibit the auto-proteolytic activity of an HCV NS2/3 protease.

8. A method according to claim 7 comprising measuring inhibition of the dimerisation of said polypeptides.

9. A method according to claim 7 comprising measuring inhibition of the HCV NS2/3 protease auto-proteolytic activity of said polypeptides.

10. A method according to claim 9, wherein the C-terminal residue of the fragment is the amino acid that is at position 1206 in the HCV NS2/3 protease precursor.

11. A method according to claim 10, wherein the N-terminal residue of the fragment is the amino acid that is at position 903 in the HCV NS2/3 protease precursor.

12. A method according to claim 10, wherein the N-terminal residue of the fragment is the amino acid that is at position 907 in the HCV NS2/3 protease precursor.

13. A method for testing the ability of an agent to inhibit the auto-proteolytic activity of an HCV NS2/3 protease, comprising:
(a) bringing a test agent into contact with a polypeptide according to claim 5 or a homodimer of two said polypeptides; and
(b) measuring at least one of either:
(i) homodimer formation of two said polypeptides as an indication of the ability of the agent to inhibit HCV NS2/3 protease activity, wherein in the absence of said agent homodimer formation occurs, or
(ii) HCV NS2/3 protease auto-proteolytic activity as an indication of the ability of the agent to inhibit HCV NS2/3 protease activity, wherein in the absence of said agent NS2/3 protease activity is retained,
thereby determining the ability of the agent to inhibit the auto-proteolytic activity of an HCV NS2/3 protease.

14. A method according to claim 13 comprising measuring inhibition of the HCV NS2/3 protease auto-proteolytic activity of said polypeptides.

15. An assay method for testing the ability of an agent to inhibit the auto-proteolytic activity of an HCV NS2/3 protease, comprising:
(a) bringing a test agent into contact with a polypeptide according to claim 6 or a homodimer of two said polypeptides; and
(b) measuring at least one of either:
(i) homodimer formation of two said polypeptides as an indication of the ability of the agent to inhibit HCV NS2/3 protease activity, wherein in the absence of said agent homodimer formation occurs, or
(ii) HCV NS2/3 protease auto-proteolytic activity as an indication of the ability of the agent to inhibit HCV NS2/3 protease activity, wherein in the absence of said agent NS2/3 protease activity is retained,
thereby determining the ability of the agent to inhibit the auto-proteolytic activity of an HCV NS2/3 protease.

16. A method according to claim 15 comprising measuring inhibition of the HCV NS2/3 protease auto-proteolytic activity of said polypeptides.

* * * * *

SEQUENCE LISTING

<160> NUMBER OF SEQ ID NOS: 32

<210> SEQ ID NO 1
<211> LENGTH: 54
<212> TYPE: DNA
<213> ORGANISM: Artificial Sequence
<220> FEATURE:
<223> OTHER INFORMATION: Primer

<400> SEQUENCE: 1
ttggaattcc tacttcttct tcttgctagc tctcatggtt gtctctaggt tctc          54

<210> SEQ ID NO 2
<211> LENGTH: 49
<212> TYPE: DNA
<213> ORGANISM: Artificial Sequence
<220> FEATURE:
<223> OTHER INFORMATION: Primer

<400> SEQUENCE: 2
ggccacccac caccaccacc accacatgga ccgagagatg gctgcatcg               49

<210> SEQ ID NO 3
<211> LENGTH: 45
<212> TYPE: DNA
<213> ORGANISM: Artificial Sequence
<220> FEATURE:
<223> OTHER INFORMATION: Primer

<400> SEQUENCE: 3
ctacttcttc ttcttgctag cccgcatggt agtttccata gactc                   45

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
accgagagat ggctgcatcg tgcgg                                         25

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
caggctggca tgactagagt gccg                                          24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
actagagtgc cgtactttgt acgc                                          24

<210> SEQ ID NO 7
<211> LENGTH: 25

```
<212> TYPE: DNA
<213> ORGANISM: Artificial Sequence
<220> FEATURE:
<223> OTHER INFORMATION: Primer

<400> SEQUENCE: 7
tacgcgctca ggggctcatc cgtgc                                         25

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
atccgtgcat gcatgttagt gcgg                                          24

<210> SEQ ID NO 9
<211> LENGTH: 42
<212> TYPE: DNA
<213> ORGANISM: Artificial Sequence
<220> FEATURE:
<223> OTHER INFORMATION: Primer

<400> SEQUENCE: 9
caccaccacc accaccacat ccgtgcatgc atgttagtgc gg                      42

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
ctaaaggagc cgccacccct gtagacc                                       27

<210> SEQ ID NO 11
<211> LENGTH: 27
<212> TYPE: DNA
<213> ORGANISM: Artificial Sequence
<220> FEATURE:
<223> OTHER INFORMATION: Primer

<400> SEQUENCE: 11
ctaccgcatg gtagtttcca tagactc                                       27

<210> SEQ ID NO 12
<211> LENGTH: 44
<212> TYPE: DNA
<213> ORGANISM: Artificial Sequence
<220> FEATURE:
<223> OTHER INFORMATION: Primer

<400> SEQUENCE: 12
tgcatcatca tcatcatcat caggctggca tgactagagt gccg                    44

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
```

-continued tgcaggctgg catgactaga gtgccg                                    26

<210> SEQ ID NO 14
<211> LENGTH: 44
<212> TYPE: DNA
<213> ORGANISM: Artificial Sequence
<220> FEATURE:
<223> OTHER INFORMATION: Primer

<400> SEQUENCE: 14
tgcatcatca tcatcatcat actagagtgc cgtactttgt acgc                44

<210> SEQ ID NO 15
<211> LENGTH: 26
<212> TYPE: DNA
<213> ORGANISM: Artificial Sequence
<220> FEATURE:
<223> OTHER INFORMATION: Primer

<400> SEQUENCE: 15
tgactagagt gccgtacttt gtacgc                                    26

<210> SEQ ID NO 16
<211> LENGTH: 47
<212> TYPE: DNA
<213> ORGANISM: Artificial Sequence
<220> FEATURE:
<223> OTHER INFORMATION: Primer

<400> SEQUENCE: 16
ccacccacca ccaccaccac cacctggaca cggaggtggc cgcgtcg             47

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
aggttgctgc cgcccatcac ggcg                                      24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
cgccgtgatg ggcggcagca acct                                      24

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
gtgtataacg ctctcacccc tctgc                                     25

<210> SEQ ID NO 20
<211> LENGTH: 25
<212> TYPE: DNA
<213> ORGANISM: Artificial Sequence

```
<220> FEATURE:
<223> OTHER INFORMATION: Primer

<400> SEQUENCE: 20
gcagaggggt gagagcgtta tacac                                              25

<210> SEQ ID NO 21
<211> LENGTH: 33
<212> TYPE: DNA
<213> ORGANISM: Artificial Sequence
<220> FEATURE:
<223> OTHER INFORMATION: Primer

<400> SEQUENCE: 21
acgtacgtat atgacgctct tactccactg cgg                                     33

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22
ccgcagtgga gtaagagcgt catatacgta cgt                                     33

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
cggctccttc cgcctatcac ggcc                                               24

<210> SEQ ID NO 24
<211> LENGTH: 24
<212> TYPE: DNA
<213> ORGANISM: Artificial Sequence
<220> FEATURE:
<223> OTHER INFORMATION: Primer

<400> SEQUENCE: 24
ggccgtgata ggcggaagga gccg                                               24

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
gcagacaccg cggccgctgg ggacatcatc                                         30

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
ggctcatctg gtggttacaa tattttatca ccagagccg                               39
```

-continued

```
<210> SEQ ID NO 27
<211> LENGTH: 28
<212> TYPE: DNA
<213> ORGANISM: Artificial Sequence
<220> FEATURE:
<223> OTHER INFORMATION: Primer

<400> SEQUENCE: 27
ctgtgactgg tgacccgtca accaagtc                                          28

<210> SEQ ID NO 28
<211> LENGTH: 4
<212> TYPE: PRT
<213> ORGANISM: Hepatitis C Virus

<400> SEQUENCE: 28

Met His His His
 1

<210> SEQ ID NO 29
<211> LENGTH: 6
<212> TYPE: PRT
<213> ORGANISM: Artificial Sequence
<220> FEATURE:
<223> OTHER INFORMATION: C-terminal extension

<400> SEQUENCE: 29

Ala Ser Lys Lys Lys Lys
 1               5

<210> SEQ ID NO 30
<211> LENGTH: 4
<212> TYPE: PRT
<213> ORGANISM: Hepatits C Virus

<400> SEQUENCE: 30

Ala Pro Ile Thr
 1

<210> SEQ ID NO 31
<211> LENGTH: 17
<212> TYPE: PRT
<213> ORGANISM: Artificial Sequence
<220> FEATURE:
<223> OTHER INFORMATION: Pep4AK
<220> FEATURE:
<221> NAME/KEY: AMIDATION
<222> LOCATION: (17)...(17)

<400> SEQUENCE: 31

Lys Lys Lys Gly Ser Val Val Ile Val Gly Arg Ile Ile Leu Ser Gly
 1               5                  10                  15

Arg

<210> SEQ ID NO 32
<211> LENGTH: 10
<212> TYPE: PRT
<213> ORGANISM: Artificial Sequence
<220> FEATURE:
<223> OTHER INFORMATION: Internally quenched fluorogenic NS3 substrate

<400> SEQUENCE: 32

Asp Asp Ile Val Pro Cys Ser Met Ser Lys
 1               5                  10
```